United States Patent
Conklin et al.

(10) Patent No.: US 9,848,984 B2
(45) Date of Patent: *Dec. 26, 2017

(54) METHODS OF ANCHORING CARDIAC IMPLANTS USING KNOTLESS SUTURE FASTENERS

(71) Applicant: Edwards Lifesciences Corporation, Irvine, CA (US)

(72) Inventors: Brian S. Conklin, Orange, CA (US); Louis A. Campbell, Santa Ana, CA (US); Salvador Marquez, Foothill Ranch, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 345 days.

This patent is subject to a terminal disclaimer.

(21) Appl. No.: 14/797,162

(22) Filed: Jul. 12, 2015

(65) Prior Publication Data
US 2015/0320414 A1    Nov. 12, 2015

Related U.S. Application Data

(63) Continuation of application No. 13/719,009, filed on Dec. 18, 2012, now Pat. No. 9,078,645.

(Continued)

(51) Int. Cl.
*A61B 17/04* (2006.01)
*A61F 2/24* (2006.01)

(52) U.S. Cl.
CPC ........ *A61F 2/2427* (2013.01); *A61B 17/0401* (2013.01); *A61B 17/0469* (2013.01); *A61B 17/0483* (2013.01); *A61B 17/0487* (2013.01); *A61F 2/2412* (2013.01); *A61F 2/2466* (2013.01); *A61B 2017/0488* (2013.01); *A61B 2017/0496* (2013.01)

(Continued)

(58) Field of Classification Search
CPC .............. A61B 17/122; A61B 17/1222; A61B 17/1227; A61B 17/128; A61B 17/1285;

(Continued)

(56) References Cited

U.S. PATENT DOCUMENTS

| 1,243,105 A | 10/1917 | Richardson |
| 4,997,433 A | 3/1991 | Goble et al. |

(Continued)

FOREIGN PATENT DOCUMENTS

| EP | 0519703 | 12/1992 |
| EP | 0635241 | 1/1995 |
| EP | 0967940 | 1/2000 |

OTHER PUBLICATIONS

International search report for PCT US 2012/070547, Jun. 27, 2013.*

(Continued)

*Primary Examiner* — David C Eastwood
(74) *Attorney, Agent, or Firm* — Guy Cumberbatch; Pui Tong Ho

(57) ABSTRACT

Devices and methods for securing prostheses such as heart valves or annuloplasty rings with sutures and without using knots are disclosed. The devices are particularly well suited for traditional surgery or minimally invasive surgery, and improve the ease of implantation by eliminating surgical knots a clinician would normally tie in the limited space in and around the implant site. The devices have opposed the clamp halves surrounded by a coil spring. Sutures pass between the clamp halves and the coil spring has an inner coil diameter sufficient to compress the sutures between the clamp. A retention member positioned between the clamp halves maintains a minimum space and therebetween to enable the locking device to be slid along the sutures into position, and to adjust the tension of the sutures therethrough. A delivery tool may be used to deliver and deploy the locking devices.

20 Claims, 18 Drawing Sheets

Related U.S. Application Data

(60) Provisional application No. 61/639,759, filed on Apr. 27, 2012, provisional application No. 61/577,255, filed on Dec. 19, 2011.

(58) Field of Classification Search
CPC ............ A61B 17/0401; A61B 17/0487; A61B 2017/0488; A61B 2017/0409; A61B 2017/0422; A61B 2017/0424; A61B 2017/043; A61B 2017/0432; A61B 2017/0443; A61B 2017/0445; A61B 2017/0446; A61B 2017/0448; A61B 2017/045; A61B 2017/0454; A61B 2017/0456; F16G 11/00; F16G 11/10; F16G 11/101; F16G 11/105; F16L 3/10; F16L 3/1203; F16L 3/1211; F16L 33/10; H02G 3/32; A61F 2/2412; A61F 2/2427; A61F 2/2466
USPC .................. 606/142–144, 151, 157, 232
See application file for complete search history.

(56) References Cited

U.S. PATENT DOCUMENTS

| | | | |
|---|---|---|---|
| 5,593,424 A * | 1/1997 | Northrup, III | A61B 17/0401 128/898 |
| 5,681,351 A | 10/1997 | Jamiolkowski et al. | |
| 6,066,160 A * | 5/2000 | Colvin | A61B 17/0487 606/151 |
| 7,875,056 B2 * | 1/2011 | Jervis | A61B 17/0487 24/115 M |
| 9,078,645 B2 * | 7/2015 | Conklin | A61B 17/0401 |
| 9,078,652 B2 * | 7/2015 | Conklin | A61B 17/0487 |
| 9,498,202 B2 * | 11/2016 | Jafari | A61B 17/0401 |
| 9,504,466 B2 * | 11/2016 | Conklin | A61B 17/0487 |
| 2002/0068949 A1 * | 6/2002 | Williamson, IV | A61B 17/0469 606/151 |
| 2002/0128708 A1 * | 9/2002 | Northrup, III | A61F 2/2445 623/2.37 |
| 2003/0195563 A1 | 10/2003 | Foerster | |
| 2006/0271105 A1 | 11/2006 | Foerster et al. | |
| 2007/0021781 A1 * | 1/2007 | Jervis | A61B 17/0487 606/232 |
| 2008/0065203 A1 * | 3/2008 | Khalapyan | A61F 2/2445 623/2.11 |
| 2009/0082792 A1 | 3/2009 | Koyfman et al. | |
| 2009/0222029 A1 * | 9/2009 | Gordin | A61B 1/32 606/151 |
| 2010/0023128 A1 | 1/2010 | Malberg | |
| 2010/0331972 A1 * | 12/2010 | Pintor | A61F 2/2409 623/2.11 |

OTHER PUBLICATIONS

International preliminary report on patentablility Chapter I for PCT 2012/070547, Jun. 24, 2014.*

* cited by examiner

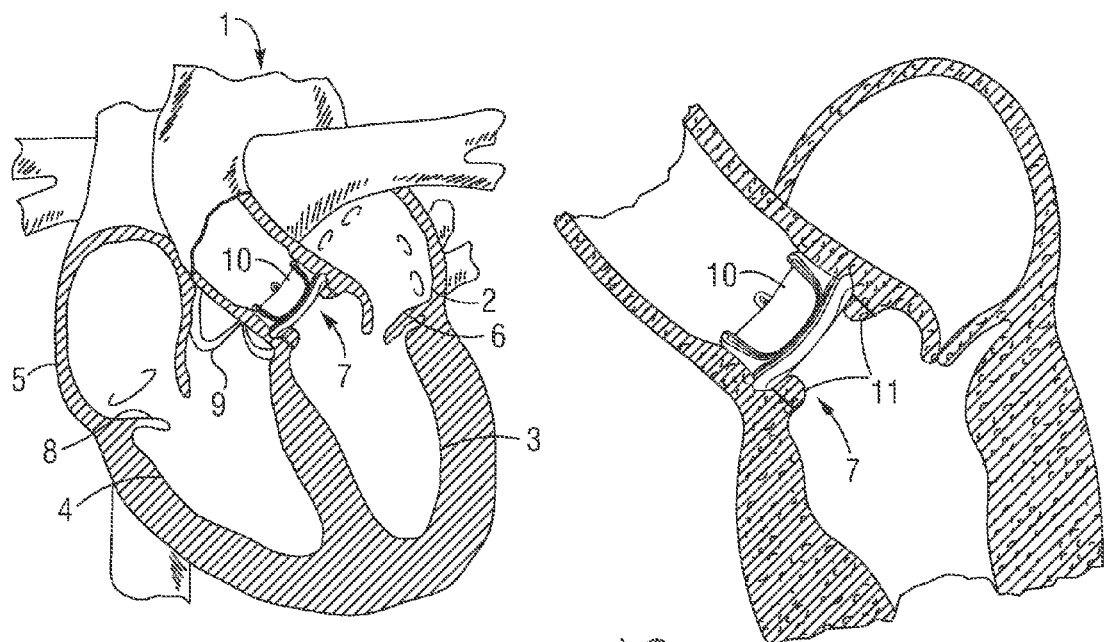
FIG. 1
(PRIOR ART)
FIG. 2
(PRIOR ART)
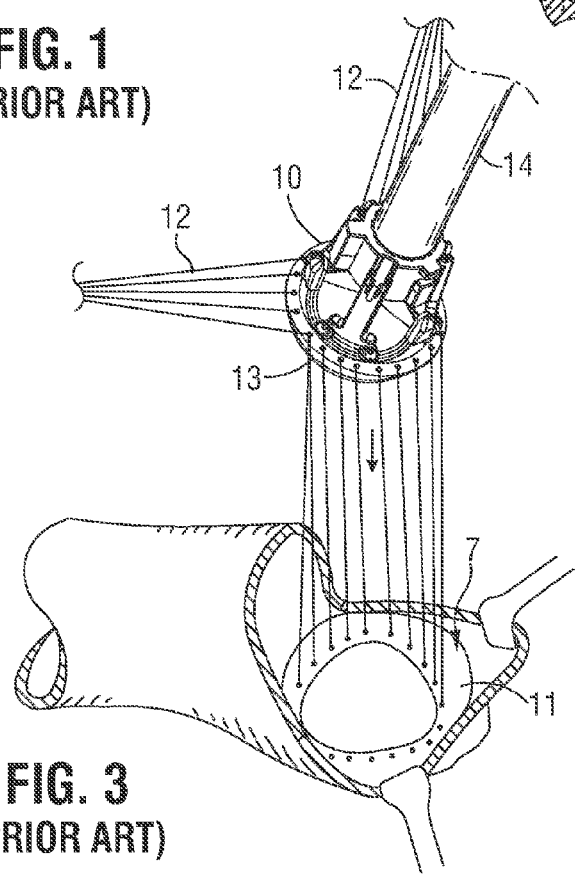
FIG. 3
(PRIOR ART)

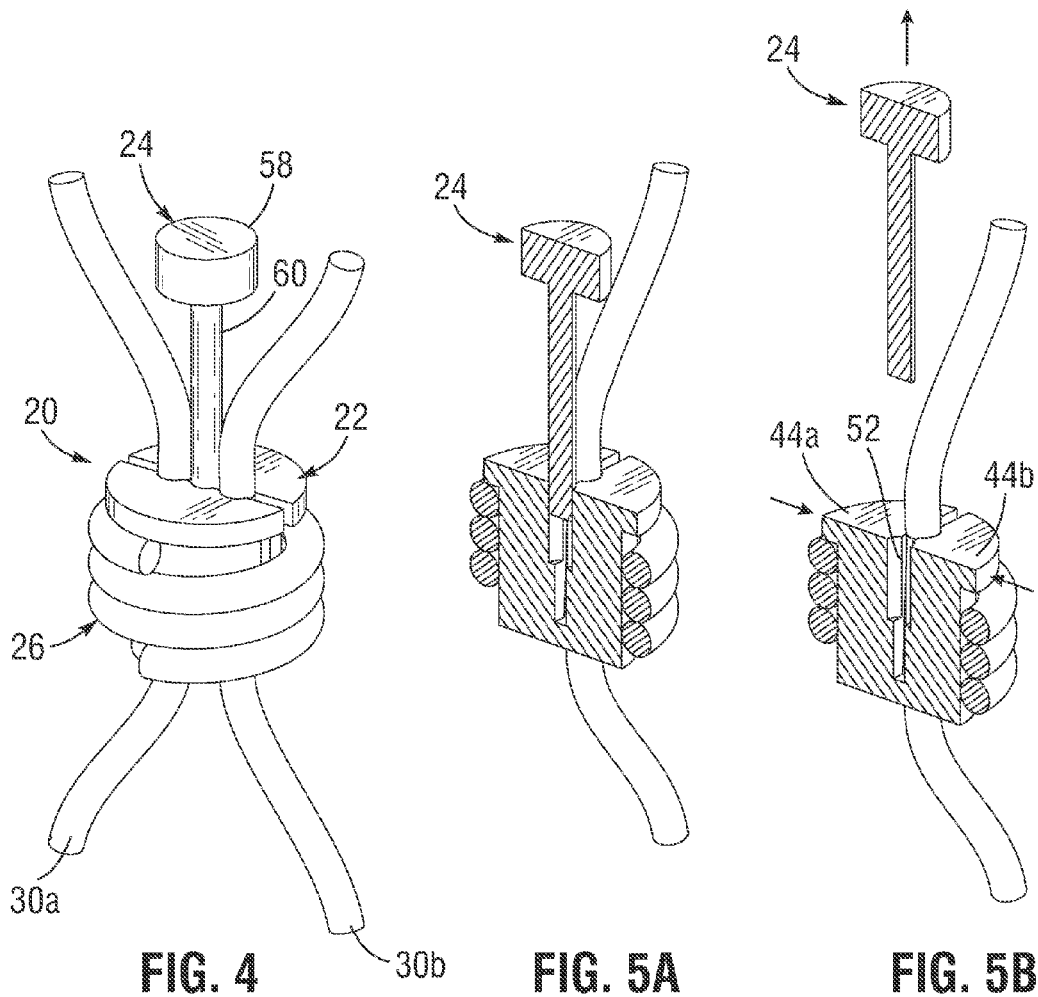

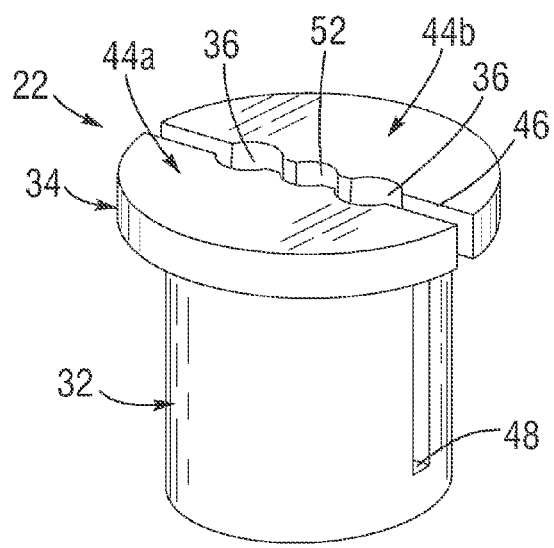 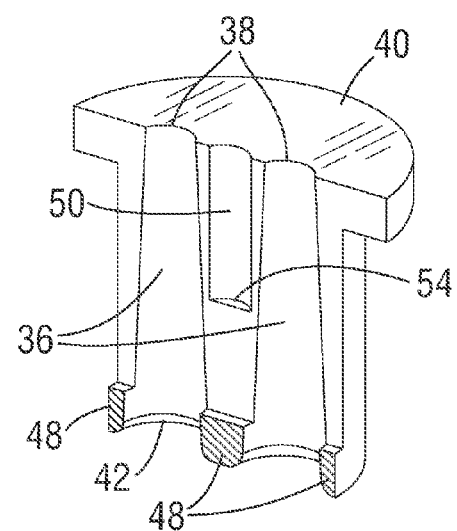
FIG. 6A   FIG. 6B
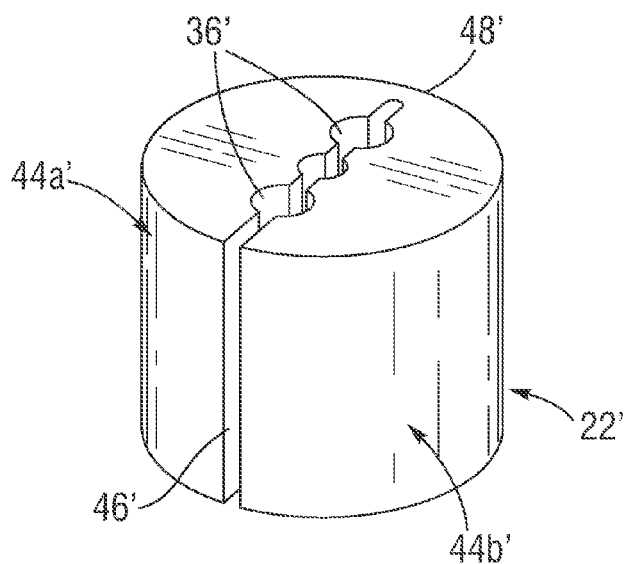
FIG. 7

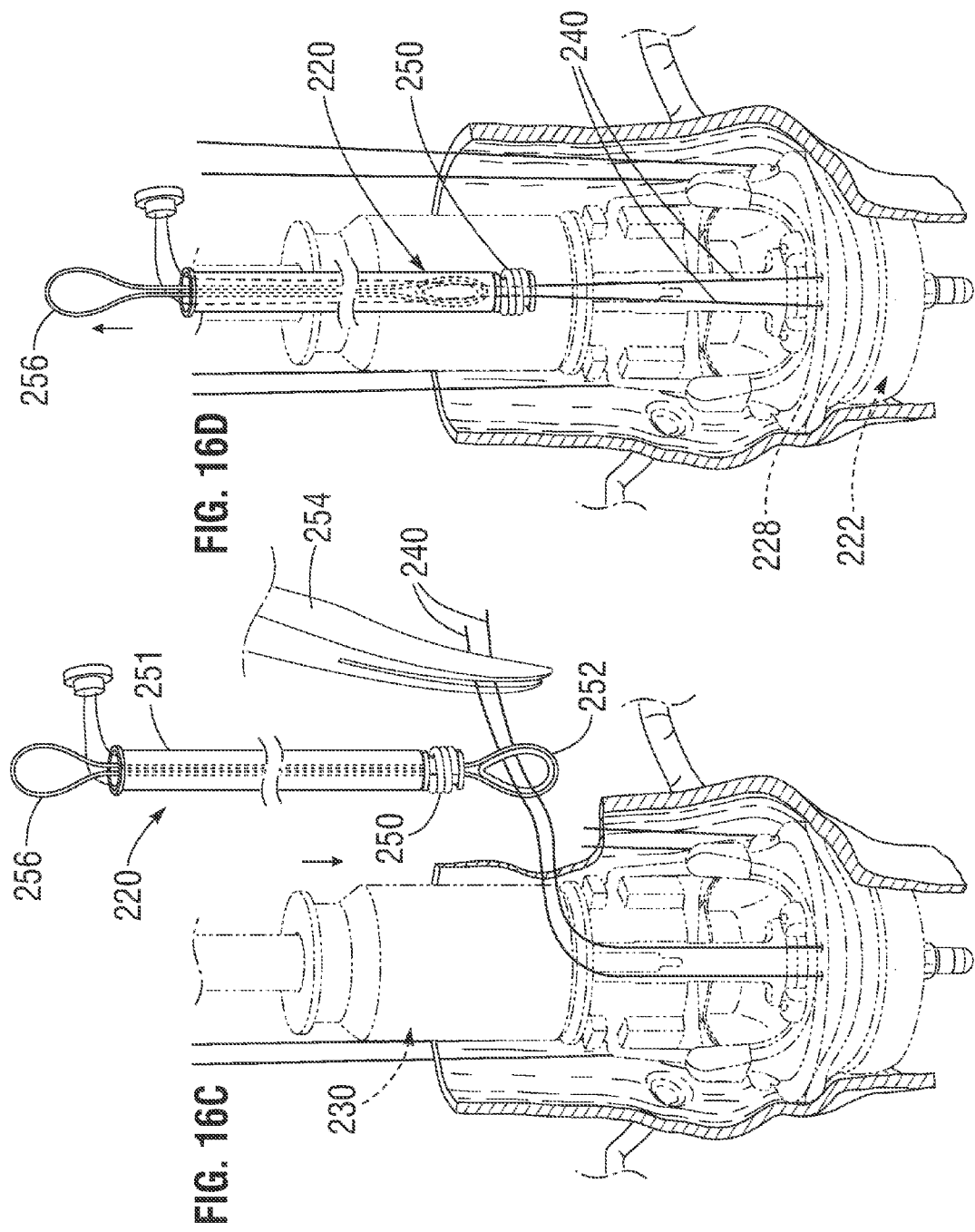

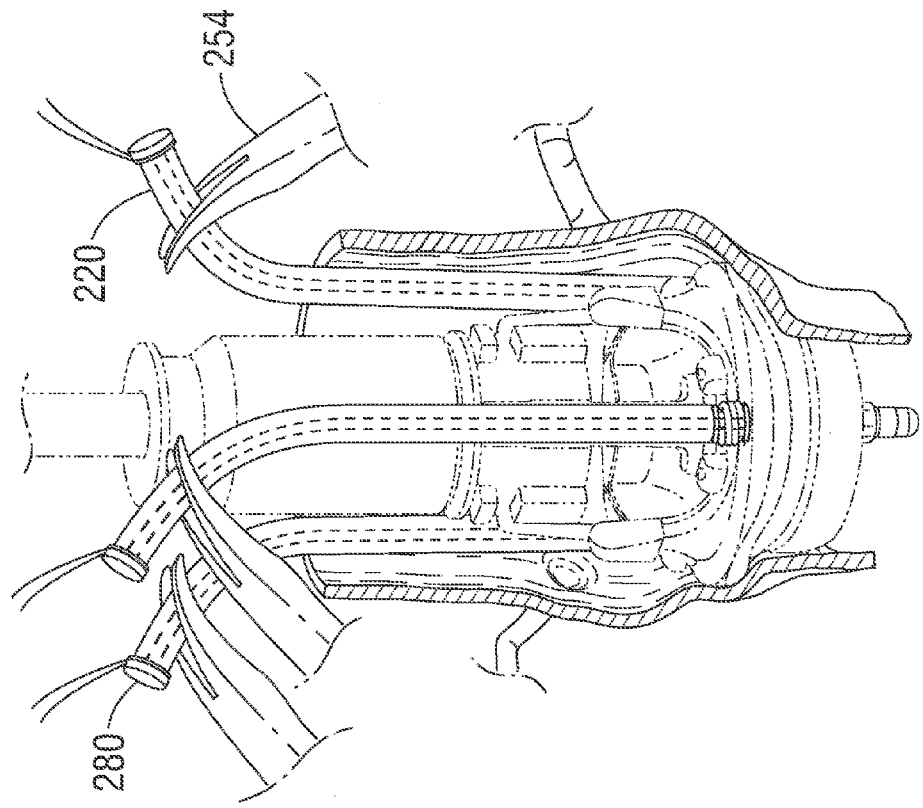
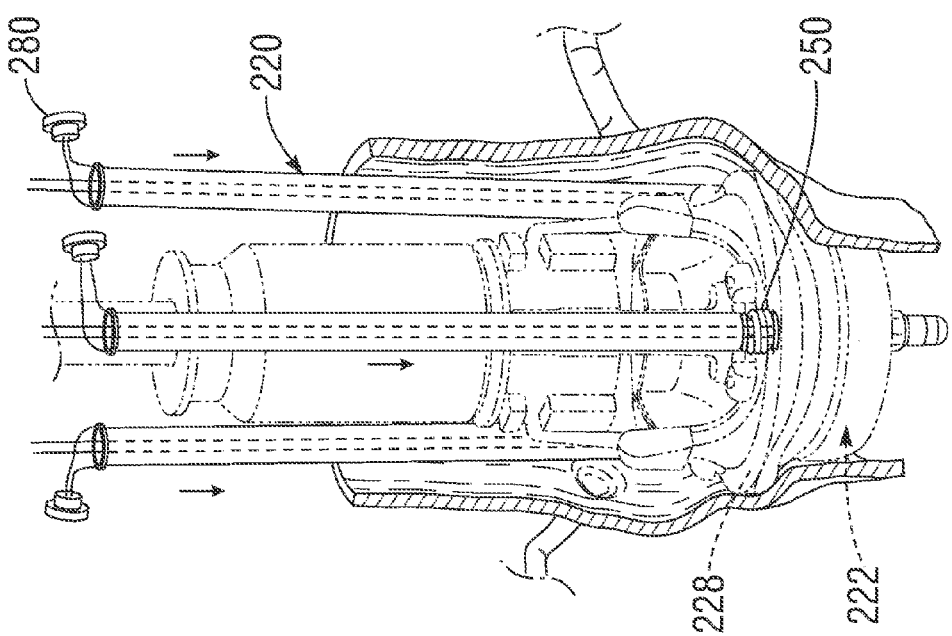

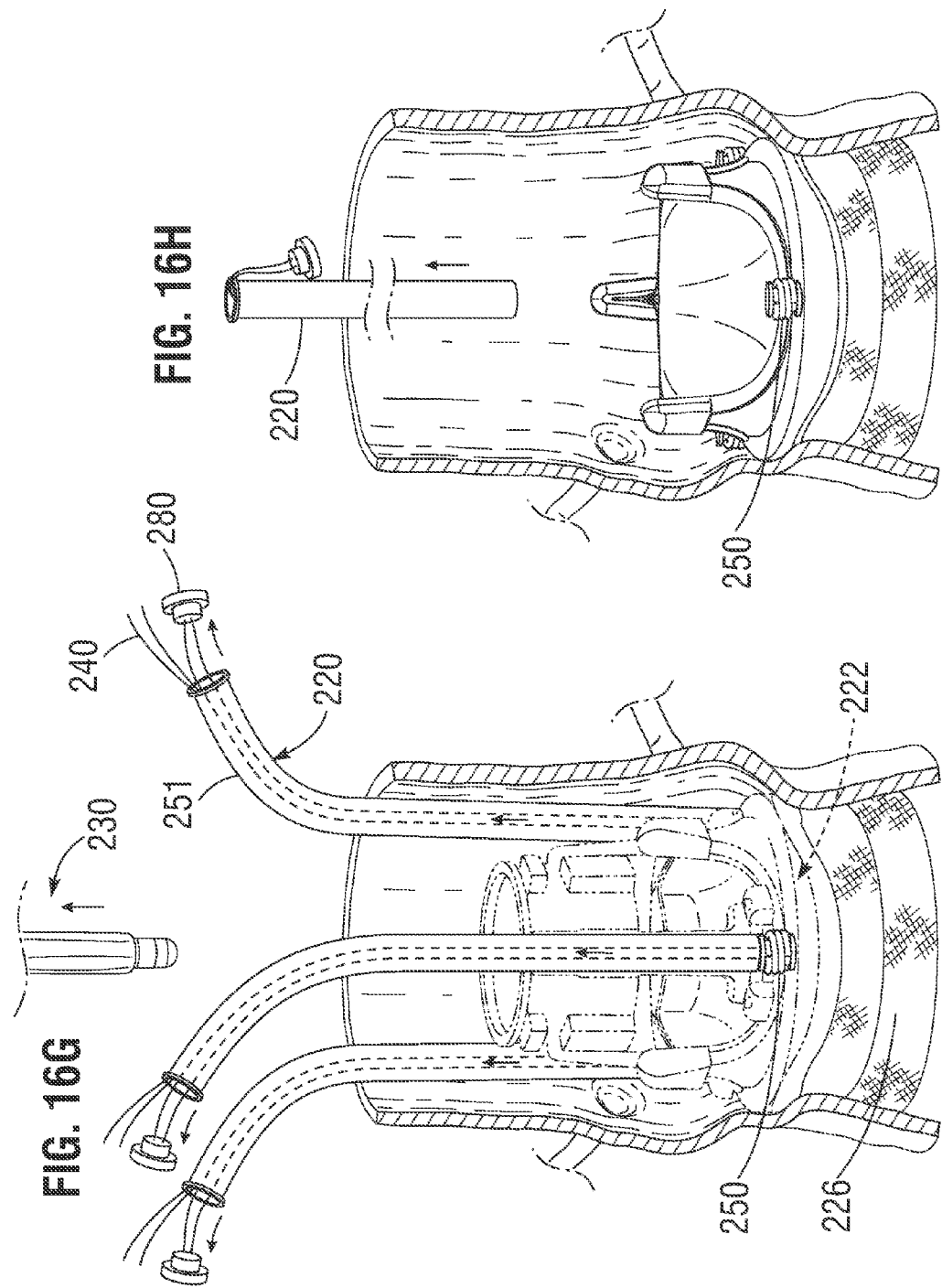

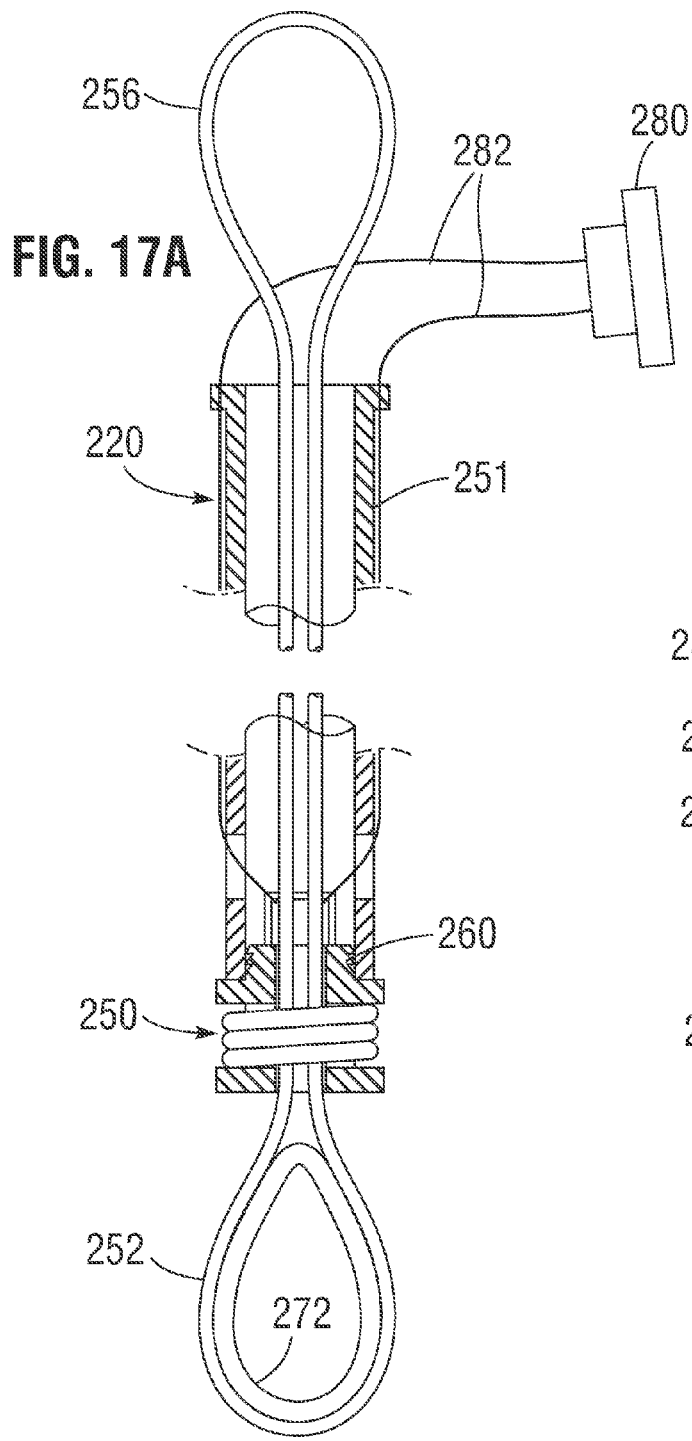

FIG. 18
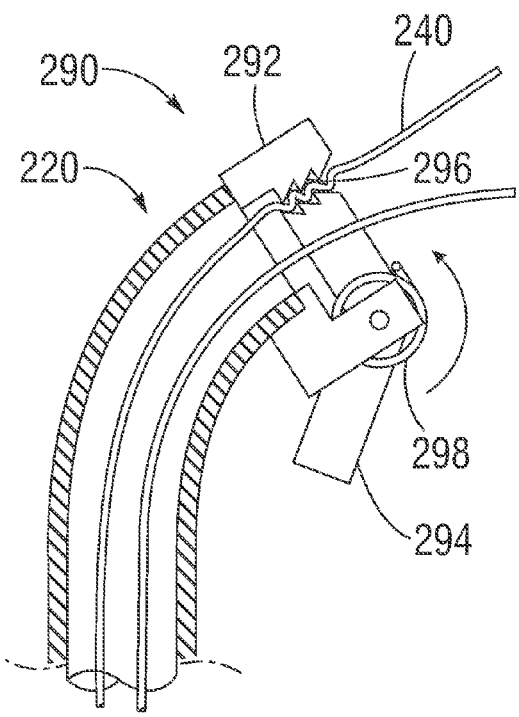
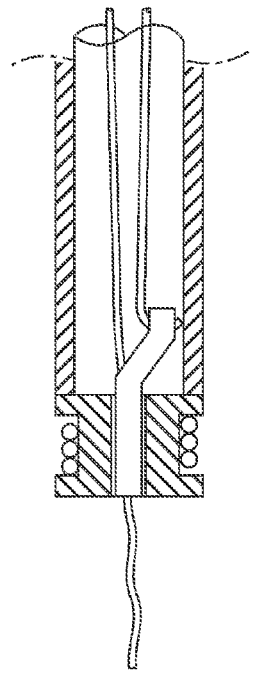
FIG. 19
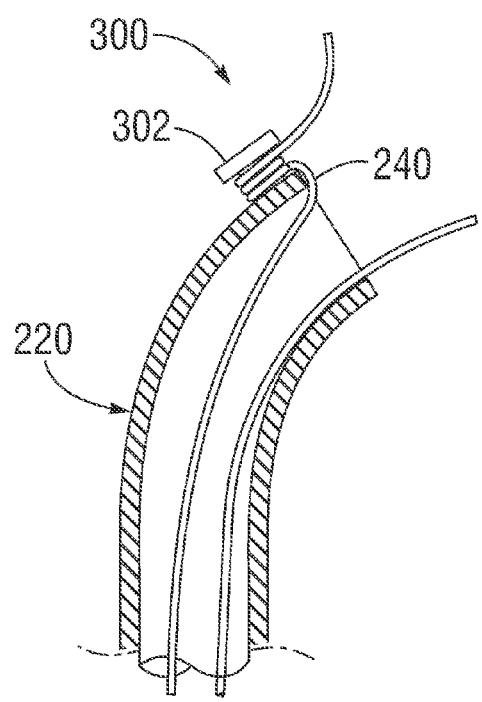
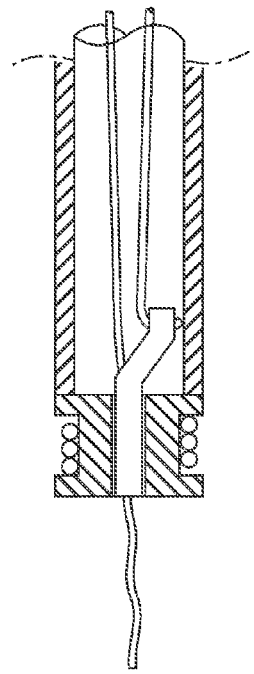

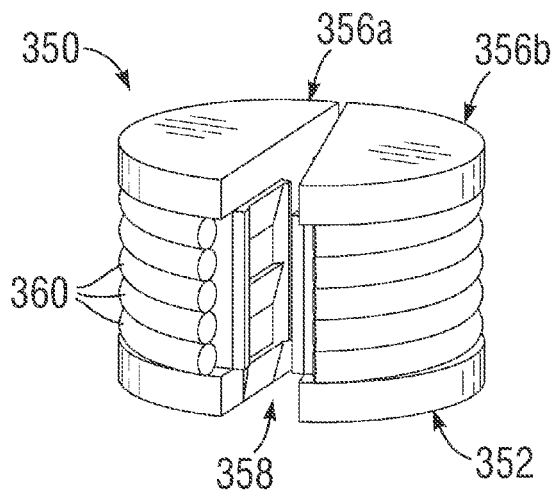
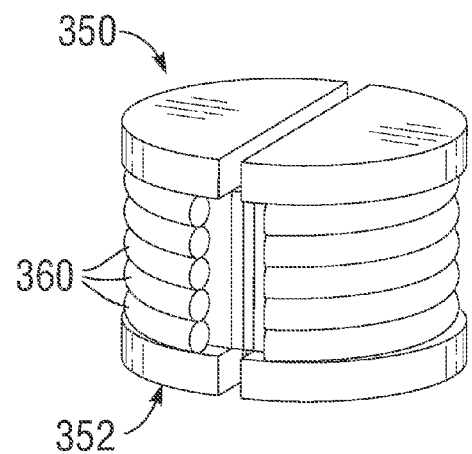
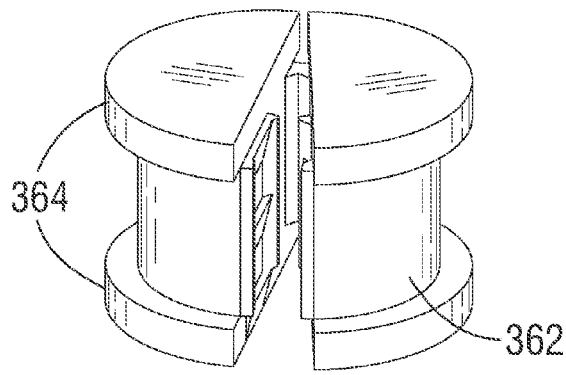
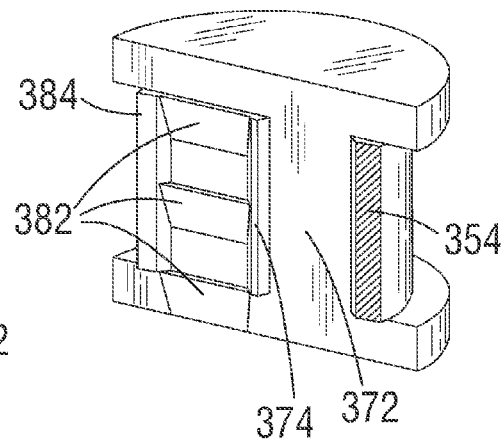
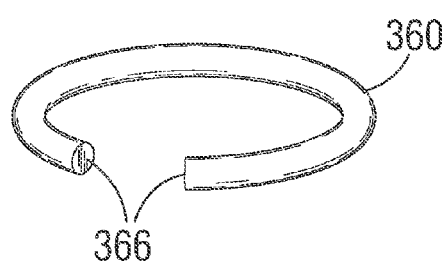

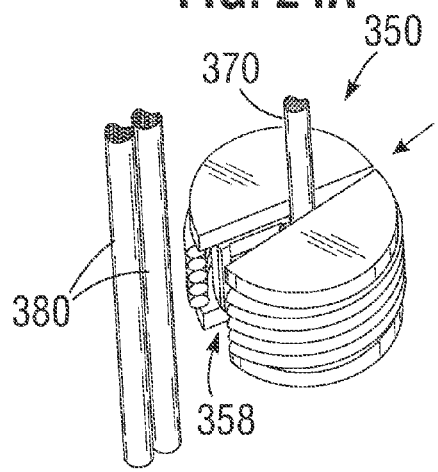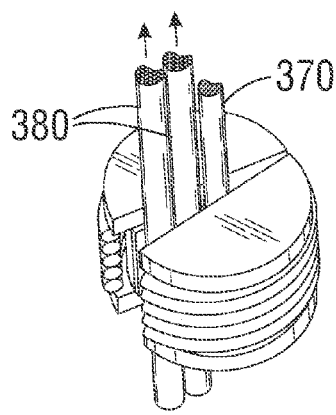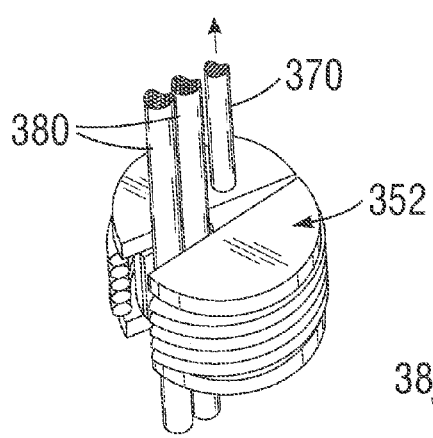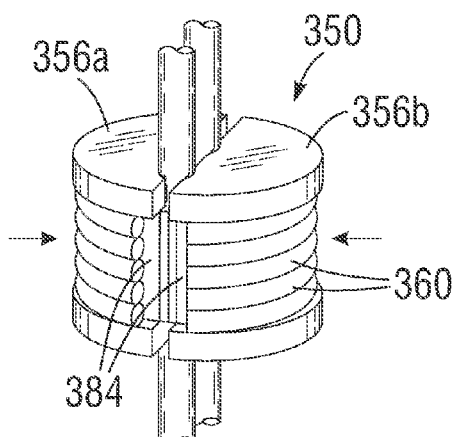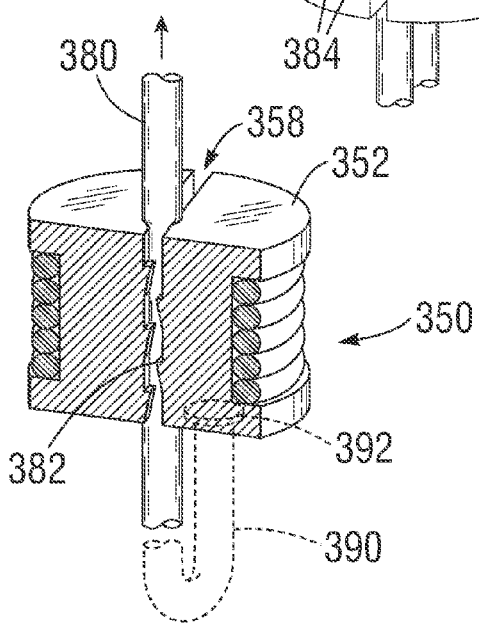

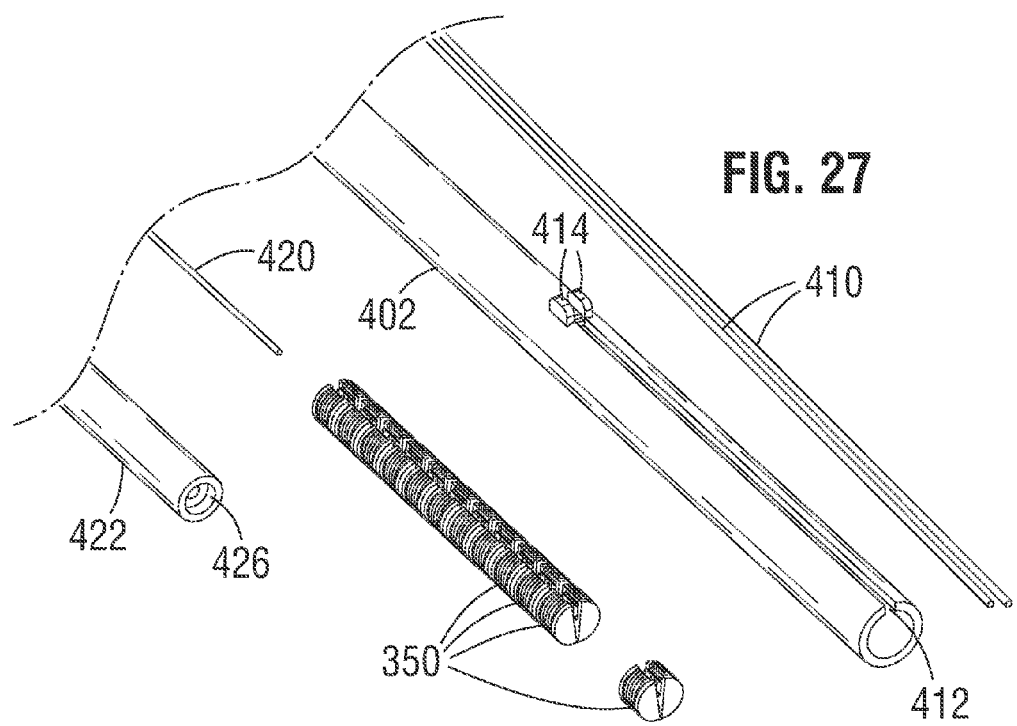
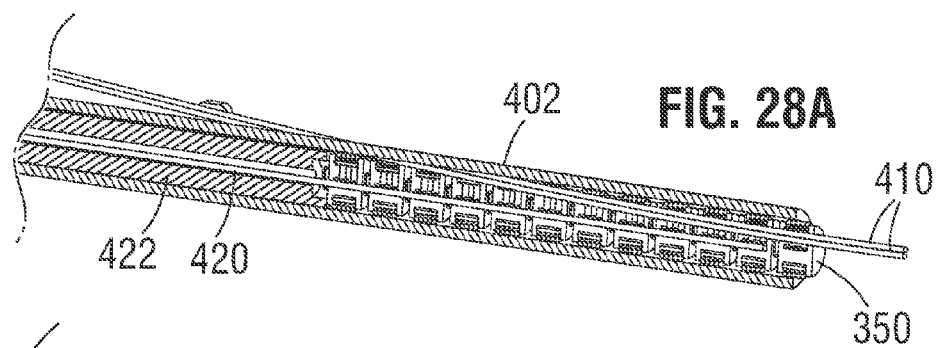
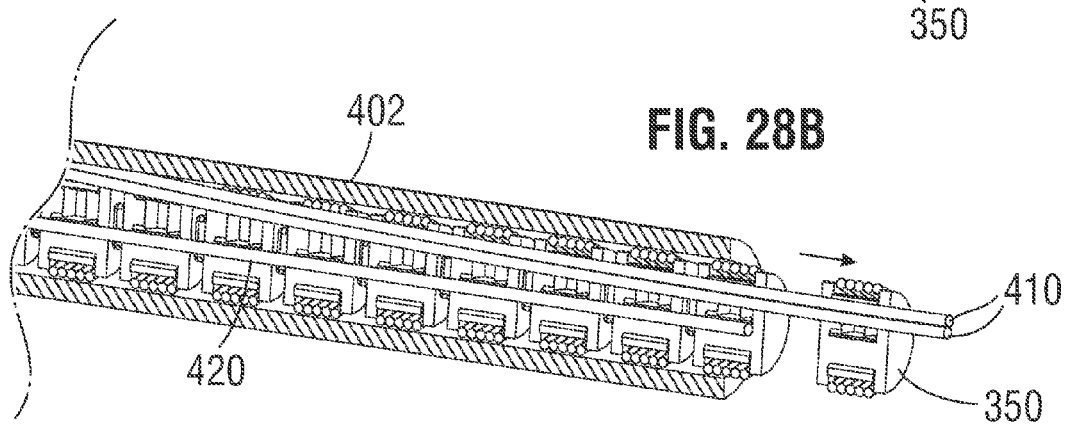

METHODS OF ANCHORING CARDIAC IMPLANTS USING KNOTLESS SUTURE FASTENERS

RELATED APPLICATIONS

The present application is a continuation of U.S. application Ser. No. 13/719,009, filed Dec. 18, 2012, which in turn claims priority to U.S. Provisional Application Ser. Nos. 61/639,759, Filed Apr. 27, 2012, and 61/577,255, Filed Dec. 19, 2011, the entire disclosures of which are incorporated by reference.

FIELD OF THE INVENTION

The present invention relates to devices and methods for securing prosthetic implants to soft tissue and, more particularly, to methods for anchoring prostheses inside or near the heart using sutures without knots.

BACKGROUND OF THE INVENTION

Sutures are used for a variety of surgical purposes, such as approximation of tissue and ligation of tissue. When placing sutures, the strand of suture material to be used typically has a needle affixed to one end which is passed (looped) through the tissue to be approximated or ligated, forming a stitch. The stitch is then tensioned appropriately, and the two free ends of the suture loop, the needle end and the non-needle end, are knotted to retain the desired tension in the stitch. Forming knots in suture during open surgery is a simple matter, though time-consuming, but forming knots in sutures during endoscopic surgery can require two surgeons to cooperate in a multi-step process which is performed with multiple instruments to pass the needle and suture back and forth to tie the suture knot.

Within the prior art there exists a need for devices and methods that reduce the time required to secure a heart valve repair prosthesis in place. To repair or replace a defective valve, clinicians can perform traditional open heart surgery or can utilize a minimally invasive or transcatheter technique. Traditional open heart surgery involves administering anesthesia and putting a patient on cardio-pulmonary bypass. A clinician cuts open the chest to access the heart, and then typically excises the defective native valve leaflets leaving the annulus in place. The clinician places sutures in the annulus or other tissue near the heart valve, and threads the free ends of each loop of the sutures through a sewing cuff on the heart valve prosthesis. The heart valve is then "parachuted" into place by sliding it down the suture free ends until it rests on the annulus. The free ends of each suture loop are tied together on the proximal side of the heart valve with multiple knots to prevent the sutures from backing out. Normally, this process entails about 5-10 knots on each of the 12-20 sutures used per implant, which lengthens the time a patient is on cardio-pulmonary bypass and under anesthesia. There is a direct correlation between time spent on bypass and poor outcomes, and thus any reduction in surgical time that a patient undergoes would be beneficial. Implantation of an annuloplasty ring follows a similar procedure except that the native valve is typically left in place. The annuloplasty ring is sutured in place to reshape or repair the valve annulus and improve native heart valve leaflet coaptation.

There also exists a need to make it easier to secure a heart valve repair prosthesis in place. Currently, a clinician must work in the limited space near the heart to tie knots in sutures. This is a cumbersome process that benefits from a clinician of great dexterity and patience. In a minimally invasive surgery the clinician must use tools that can be passed through a small incision, thus making the tying of knots even more difficult. To implant the prosthesis, a clinician makes a small incision in the chest and uses special tools to pass the heart valve repair prosthesis through the incision. An example of a minimally invasive heart valve repair procedure is transapical aortic valve replacement.

Suture locking devices that eliminate the need to tie knots in order to speed up heart valve replacement are known, as are suture locking devices in general. Suture retainers or locks are used in place of suture knots to prevent passage of a suture end into and through tissue and to maintain the tension applied to the suture material during the suturing procedure. Suture clips and other suture retainers are described in the following publications: U.S. Pat. Nos. 6,066,160, 6,475,230, 7,862,584, 7,875,056, 8,100,923, and 8,105,355.

Despite the existence of knotless suture locking devices in the art, there is a need for improved devices that enable accurate tensioning of the suture and are simple to use. Some of the prior devices utilize a wedge-type system in which a wedge or opposed wedge surfaces are brought together to clamp on the suture. Some of these devices are susceptible to changes in the magnitude of tension in the suture as they are being locked, either loosening or tightening the suture, while others may work loose if there is no additional mechanism to hold them in place. Some devices such as U.S. Pat. No. 7,862,584 utilize a clamping system having a tortuous path for the suture, which are difficult to thread and also may work loose. Another type of suture locking device shown in U.S. Pat. No. 7,235,086 makes use of a plastically deformable member to capture the suture therein. This device depends on accurate deformation of the clamping member, which might permit the suture to slip loose if insufficiently deformed.

SUMMARY OF THE INVENTION

The present invention provides an improved suture locking device for securing heart valve repair or replacement prostheses in or near the heart. The apparatus and methods are particularly well suited for traditional surgery or minimally invasive surgery. The devices disclosed herein eliminate the need for surgical knots thus reducing surgical time and exposure. Further, the devices improve the ease of implantation because the clinician need not tie knots in the limited space in and around the heart. Finally, the suture locking devices are simple to install and their actuation does not affect suture tension.

In accordance with one preferred aspect, the present application provide a system for locking a device on one or more sutures, comprising one or more sutures each having a thickness, a bifurcated locking clamp, a biasing member positioned on the outside of the locking clamp, and a retention member positioned between the clamp halves. The locking clamp includes a pair of substantially similar clamp halves each having an exterior surface and an inner surface facing the inner surface of the other clamp half to form a variable sized slot therebetween. The clamp halves are connected for movement toward or away from one another while being fixed axially with respect to one another, wherein the suture(s) extend through the slot between the inner surfaces of the clamp halves. The biasing member has a relaxed size that, in the absence of an object in the slot, urges the inner surfaces of the clamp halves together such that the slot has a width smaller than the suture thickness. The retention member acts against the force of the biasing member and has a thickness that maintains the slot width large enough to permit passage of the suture(s) therethrough, wherein removal of the retention member permits the biasing member to urge the inner surfaces of the clamp halves together and clamp the suture(s) therebetween.

The clamp halves may be separate elements, and they may be separate and hinged together or one piece with a living hinge therebetween. The inner surfaces of the clamp halves may include a suture channel size to receive each suture. In one embodiment, the clamp halves each includes a cutout facing a similar cutout of the other, the cutouts together defining a retention member channel for receiving the retention member. The retention member may comprise a retention pin having a head and a shaft, or it may be a bifurcated retention clip. The bifurcated retention clip may have a pair of prongs having parallel free ends that extent between the clamp halves and angled portions connecting the free ends to a bridge connecting the prongs, the bridge thus being offset from the slot between the clamp halves.

In a preferred embodiment, the clamp halves further include outward flanges on opposite axial ends that retain the biasing member in position around the locking clamp. The biasing member may be a coil spring, and the exterior surface of the clamp halves is at least partly cylindrical such that the coil spring provides a substantially uniform inward radial compressive force on the device. Alternatively, the clamp halves are hinged together on a first circumferential side such that the variable sized slot defines a variable sized opening on the side opposite the first circumferential side, and wherein the biasing member comprises a plurality of C-clips arranged around the locking clamp with their free ends located on either side of the variable sized slot opposite the first circumferential side. In one such embodiment the clamp halves are molded from a single piece of material with a living hinge on the first circumferential side. In a preferred version the inner surfaces of the clamp halves possess features to enhance friction between the clamp halves and the suture, and more preferably the inner surfaces of the clamp halves possess features to create one-way friction between the clamp halves and the suture(s). A maximum radial dimension of the bifurcated locking clamp is desirably about 2 mm or less.

A preferred system for locking a device onto at least one suture having a thickness, comprises an elongated delivery tool having a proximal end, a distal end, and a delivery tube therebetween having a lumen, the tool further including an elongated tension member that extends along the delivery tube. A suture locking device is positioned on the distal end of the delivery tool and has a bifurcated locking clamp including a pair of substantially similar clamp halves each having an exterior surface and an inner surface facing the inner surface of the other clamp half. The clamp halves are fixed axially with respect to one another but being connected for movement toward or away from one another to form a variable sized slot therebetween. The device further includes a biasing member that, in the absence of an object in the slot, urges the inner surfaces of the clamp halves together such that the slot has a width smaller than the suture thickness. A retention member positioned between the clamp halves against the force of the biasing member has a thickness that maintains the slot width large enough to permit passage of a suture therethrough. Removal of the retention member thus permits the biasing member to urge the inner surfaces of the clamp halves together and clamp the suture(s) therebetween. Wherein a distal end of the elongated tension member engages the retention member to enable tension in the tension member to apply a proximal force to the retention member. Finally, an actuator on the proximal end of the delivery tool causes relative axial displacement between the retention member and the suture locking device so as to remove the retention member from within the variable sized slot and permit the clamp halves to clamp the suture therebetween.

In a preferred embodiment, the elongated tension member and retention member are a single element defining a retention cable extending through multiple suture locking devices arranged in series within the delivery tube. Further, the actuator on the proximal end of the delivery tool desirably causes proximal displacement of the retention cable relative to the series of suture locking devices. Moreover, the system may have a pusher tube located within the delivery tube and in contact with a proximal suture locking device in the series of suture locking devices, wherein the actuator alternately causes distal displacement of both the pusher tube and the retention cable, and then proximal displacement of the retention cable relative to the series of suture locking devices and to the pusher tube.

In one version of the system, the clamp halves are hinged together on a first circumferential side such that the variable sized slot defines a variable sized opening on the side opposite the first circumferential side, and the biasing member comprises a plurality of C-clips arranged around the locking clamp with their free ends located on either side of the variable sized slot opposite the first circumferential side. If the clamp halves are hinged together, the delivery tube may have a longitudinal channel commencing at a distal tip and extending a distance axially along the tube, the series of suture locking devices being oriented so that their variable sized slots are all aligned with the longitudinal channel to permit side entry of a suture into one or more of the slots.

Alternatively, the biasing member comprises a coil spring, and the exterior surface of the clamp halves is at least partly cylindrical such that the coil spring provides a substantially uniform inward radial compressive force on the device. The system may further include a suture snare that passes from the proximal end to the distal end of the delivery tool and having a capture loop on a distal end. The capture loop extends from the lumen of the delivery tube through the variable sized slot of the suture locking device and is compressible to enable it to be pulled proximally through the slot. Another possibility is a tensioning assembly affixed to the proximal end of the delivery tool having an anchor for temporarily securing a suture that extends through the delivery tool and through the suture locking device. The tensioning assembly thus enables adjustment of the tension in the suture when secured to an implant location beyond the distal end of the delivery tool and suture locking device.

The present application also discloses a method for anchoring an implant to soft tissue, the implant having been advanced to the soft tissue down a plurality of loops of suture that are preinstalled at the soft tissue. The method involves first providing an elongated delivery tool having a proximal end and distal delivery tube, the tool further including an elongated tension member that extends along the delivery tube and that may be displaced axially from the proximal end. Two free ends of one of the suture loops are threaded through a suture locking device, the device having a bifurcated locking clamp including a pair of substantially similar clamp halves each having an exterior surface and an inner surface facing the inner surface of the other clamp half. The clamp halves are fixed axially with respect to one another while being connected for movement toward or away from one another to form a variable sized slot therebetween. The free ends extend through the slot between the inner surfaces of the clamp halves. The device further includes a biasing member that, in the absence of any other object in the slot, urges the inner surfaces of the clamp halves together such that the slot has a width smaller than the suture thickness. A retention member positioned between the clamp halves against the force of the biasing member has a thickness that maintains the slot width large enough to permit passage of the suture free ends therethrough, wherein removal of the retention member permits the biasing member to urge the inner surfaces of the clamp halves together and clamp the suture(s) therebetween. The method includes the steps of:

a. assembling the suture locking device with a distal end of the delivery tube by engaging a distal end of the elongated tension member with the retention member;

b. advancing the suture locking device on the distal end of the delivery tube down the free ends of the suture loop until the locking device contacts the implant;

c. adjusting tension in the free ends of the suture; and d. displacing the elongated tension member, proximally pulling the retention member from between the clamp halves, thus enabling the biasing member to force the clamp halves toward each suture and clamp the free ends therebetween.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 1 is a drawing of a prosthetic heart valve implanted in the aortic valve position of a human heart;

FIG. 2 is an enlarged view of the implanted heart valve of FIG. 1;

FIG. 3 is a drawing of an intermediate step in the implantation procedure of the heart valve shown in FIG. 1;

FIG. 4 is a perspective view of an exemplary suture locking device disclosed herein including a bifurcated locking clamp biased together by an exterior coil spring;

FIG. 5A is a longitudinal sectional view through the device shown in FIG. 4 with a retention pin in place, while FIG. 5B shows actuation of the device upon removal of the retention pin from a locking clamp to secure a suture therein;

FIG. 6A is a perspective view of a diametrically hinged locking clamp similar to that used in the device of FIG. 4, while FIG. 6B is a longitudinal sectional view of the locking clamp;

FIG. 7 is a perspective view of an alternative locking clamp having an axial hinge;

FIGS. 16A-16H illustrate a number of steps in an exemplary heart valve implantation procedure that utilizes a plurality of automated delivery tubes for securing suture locking devices as disclosed herein on a proximal side of the heart valve sewing ring, namely:

FIG. 16A shows a preliminary step in preparing an aortic annulus for receiving the heart valve including installation of guide sutures;

FIG. 16B shows a hybrid heart valve mounted on a distal section of a delivery handle advancing into position within the aortic annulus along the guide sutures;

FIG. 16C shows the hybrid heart valve in phantom in a desired implant position and alignment of one of a plurality of an automated delivery tubes used to install suture locking devices of the present application;

FIG. 16D shows a step in threading a pair of guide sutures through the delivery tube and through a suture locking device held thereby;

FIG. 16E shows advancement of the plurality of delivery tubes toward the hybrid heart valve until the suture locking devices abut the sewing ring thereon;

FIG. 16F shows forceps bending outward upper ends of the delivery tubes to improve access to the heart valve and implant site;

FIG. 16G shows a cloth-covered anchoring skirt on the hybrid heart valve expanded against the subvalvular wall and subsequent removal of the delivery system, as well as actuation of the delivery tubes to clamp the suture locking devices onto the guide sutures;

FIG. 16H shows detachment of the delivery tubes from the suture locking devices and removal of the tubes;

FIGS. 17A and 17B are longitudinal sectional and enlarged views of the automated delivery tube used in the procedure illustrated in FIGS. 16A-16H;

FIGS. 18 and 19 are longitudinal sectional views of alternative mechanisms for temporarily tensioning sutures to the automated delivery tubes disclosed herein;

FIGS. 20A and 20B are perspective views of an alternative "side entry" suture locking device having a bifurcated locking clamp having an axial hinge, as in FIG. 7, and biased together by exterior C-springs;

FIG. 21 shows just the bifurcated locking clamp, while FIG. 22 shows an inner wall structure of one half of the clamp and FIG. 23 shows one of the C-springs;

FIGS. 24A-24D are perspective views of a sequence of operation of the side entry suture locking device;

FIG. 25 is a perspective cross sectional view of the side entry suture locking device clamped onto a suture that is pre-attached at one end to the device, and showing how the suture(s) can be tensioned further;

FIG. 27 is an exploded perspective view of components of the side entry suture locking device delivery system;

FIGS. 28A and 28B are longitudinal sectional views through a distal end of the side entry suture locking device delivery system.

DETAILED DESCRIPTION OF THE PREFERRED EMBODIMENTS

Figure 8:
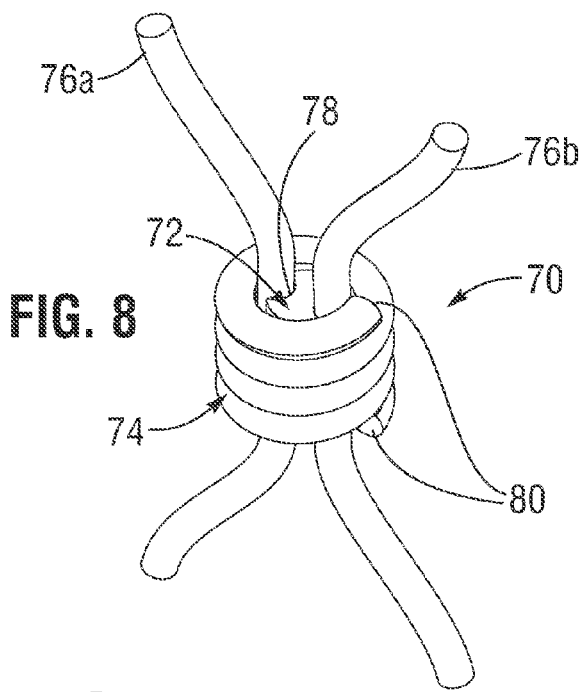
FIG. 8 is a perspective view of an alternative suture locking device of the present application.

Various suture locking devices of the present invention comprise heart valve repair or replacement prosthesis anchors that improve ease of implantation, reduce surgical exposure, and improve prosthesis attachment. It should be appreciated that the principles and aspects of the embodiments disclosed and discussed are also applicable to other types of surgical procedures, namely annuloplasty ring implant for heart valve repair. Furthermore, certain embodiments may also be used in conjunction with other medical devices or other procedures not explicitly disclosed. However, the manner of adapting the embodiments described to various other devices and functionalities will become apparent to those of skill in the art in view of the description that follows.

A schematic drawing of a surgical prosthetic heart valve implanted in the heart 1 by traditional methods is shown in FIG. 1. The left atrium 2 and the left ventricle 3 are shown separated by the mitral valve 6. The aortic valve 7 is at the outflow end of the left ventricle 3. On the opposite side of the heart, the right atrium 5 and the right ventricle 4 are shown separated by the tricuspid valve 8. The pulmonary valve 9 is at the outflow end of the right ventricle 4. An exemplary surgical prosthetic heart valve 10 is shown implanted in the aortic valve 7 position. An enlarged view of the aortic valve 7 is shown in FIG. 2. The aortic annulus 11 is a fibrous ring extending inward as a ledge into the flow orifice, and can be seen with the prosthetic heart valve 10 sutured in place above it. Prior to valve replacement, the native leaflets extend inward from the annulus 11 and coapt or meet in the flow orifice to permit flow in the outflow direction (up in FIG. 2) and prevent backflow or regurgitation toward the inflow direction (down in FIG. 2).

FIG. 3 shows one step of the traditional procedure to implant the prosthetic heart valve 10. During implantation, a clinician pre-installs sutures 12 through the annulus 11 of the aortic valve 7. While the heart valve is held on a fixture or holder 14, a clinician can thread the suture 12 free ends through a sewing ring 13 on the prosthetic heart valve 10. Thus, both free ends of each suture 12 extend out of adjacent portions of the sewing ring 13. The valve 10 is then "parachuted" down the array of sutures 12 in the direction shown and pulls the sutures 12 tight so that a seal is formed between the sewing ring 13 and the aortic annulus 11. Next, the clinician ties each suture 12 free end to another free end (typically a loop of one suture strand) securing the prosthetic heart valve 10 in place. Normally this process entails about 5-10 knots per suture and 12-20 sutures are used per implant. The ends of each suture 12 are clipped leaving a suture tail comprised of the suture used to create each knot.

Turning now to the present invention, certain efficiencies when using the suture locking devices described herein which reduce the procedure time will be explained. In the description that follows, the aortic annulus is used as the implantation site to illustrate the embodiments. The teachings of this invention can also be applied to the mitral, pulmonary, and tricuspid valves; or indeed, other valves in the body, including venous valves. Likewise, unless there is some reason such as space limitations, the suture locking devices defined herein could be utilized in other surgical contexts.

A suture locking device 20 according to one embodiment of the present invention is shown in FIG. 4. The device 20 comprises a bifurcated locking clamp 22, a retention pin 24, and an exterior coil spring 26. Two lengths of sutures 30a, 30b are shown passing longitudinally through the interior of the device 20. Typically, the two lengths of suture 30a, 30b comprise the free ends of a suture loop that has been pre-installed through soft tissue such as a heart valve annulus and passed through a heart valve sewing ring. In that configuration, the lower two suture fragments illustrated continue downward and connect in a loop, while the upper two fragments continue upward and outside of the surgical implantation site, such as through a sewing ring of a heart valve. For purposes of orientation, the upward direction in FIG. 4 shall be termed the proximal direction, while the downward direction shall be the distal direction, corresponding to the typical nomenclature used for a heart valve implantation procedure. Of course, proximal and distal are relative terms that refer to the position of the surgeon relative to the implant site, and these could be reversed depending on the particular procedure.

In any event, the suture locking device 20 defines a central axis therethrough along the proximal-distal orientation. FIGS. 6A and 6B more clearly illustrate the bifurcated locking clamp 22, which comprises a lower cylindrical portion 32 and an upper circular flange 34. A pair of generally axial suture channels 36 extend the full length of the device, as seen in FIG. 6B. Each of the suture channels 36 opens at a first aperture 38 on a top face 40 of the circular flange 34, and gradually widens to a lower aperture 42 at the bottom of the cylindrical portion 32. The suture channels 36 are centered on a diametric plane through the locking clamp 22, and their centers are spaced apart symmetrically across a central axis of the clamp.

As mentioned, the locking clamp 22 is bifurcated and forms two connected halves 44a, 44b across a variable sized slot 46 diametrically passing through the clamp in a vertical plane. The two halves 44a, 44b are joined at the lower end of the device at a hinge 48; the hinge actually comprising separated hinge areas 48 of the lower cylindrical portion 32 that connect both sides of the two suture channels 36. The hinge areas 48 therefore define a living hinge. As such, the suture channels 36 are not fully formed cylinders, but are defined by two partial conical surfaces on the inner wall of each of the halves 44a, 44b juxtaposed across the slot 46. Alternatively, a true hinge may be provided between the two halves 356.

As seen in FIGS. 6A and 6B, the inner wall of each half 44a, 44b of the clamp 22 features a partial cylindrical cutout 50 extending downward a short distance from the top face 40 of the circular flange 34; the cutouts 50 being mirror images of each other across the slot 46 so as to define a dead-end retention pin channel 52 for receiving the retention pin 24. The retention pin channel 52 terminates at a bottom ledge 54, as seen in FIG. 6B, which limits advancement of the retention pin 24 downward into the clamp slot 46. The retention pin 24 includes an enlarged head 58 and a shaft 60. The shaft 60 desirably has the same radius as the radius of the cutouts 50.

In the absence of the retention pin 24 and sutures 30a, 30b, such as seen in FIG. 6A, the two clamp halves 44a, 44b extend in parallel across the slot 46 a predetermined distance apart. In this relaxed configuration, each suture channel 36 defines a gradually increasing diameter from the upper first aperture 38 to the lower second aperture 42. Because of the connecting hinge areas 48, the second aperture 42 maintains a constant diameter throughout usage of the device 20, and is larger than the diameter of the sutures 30a, 30b. However, because of the vertically extending slot 46, the upper ends of the two halves 44a, 44b may be forced farther apart or closer together, pivoting relative to each other about the lower hinge, and thus the diameter of the first apertures 38 varies depending on the size of the slot 46.

Prior to use, the two halves 44a, 44b are forced apart so that the retention pin shaft 60 may be inserted into the retention pin channel 52, as seen in FIGS. 4 and 5A. Preferably, the device 20 is pre-assembled by the manufacturer, i.e. the retention pin 24 and coil spring 26 are pre-assembled with the clamp halves 44a, 44b. The surgeon or technician would only need to feed the sutures 30a, 30b between the clamp halves 44a, 44b at which point the device is ready to deploy manually or using a delivery tool such as described below with respect to FIGS. 9 and 10. The shaft 60 may bottom out in the pin channel 52, against the bottom ledge 54, or may be only partially inserted into the pin channel. With the retention pin 24 inserted between the two halves 44a, 44b of the locking clamp 22, the suture channels 36 are larger than the sutures 30a, 30b, permitting free passage of the sutures longitudinally through the device 20. It may be beneficial to create a nominal amount of friction between the upper end of the conical suture channels 36 and the sutures 30a, 30b to enable more controlled adjustment of the device 20 along the sutures, in which case the diameter of the first apertures 38 may be slightly smaller than the diameter of the sutures 30a, 30b when the retention pin 24 is present. Furthermore, the spacing of the cutouts 50 across the slot 46 is desirably slightly less than the diameter of the retention pin shaft 60, such that the retention pin 24 slightly wedges apart the two halves 44a, 44b.

The preceding discussion of inserting the retention pin 24 into the locking clamp 22, and passage through the device 20 of the sutures 30a, 30b desirably occurs while the coil spring 26 surrounds the clamp, and specifically the lower cylindrical portion 32 of the clamp. The coil spring 26 has a relaxed inside diameter that is smaller than the diameter of the lower cylindrical portion 32 of locking clamp 22. As such, the coil spring 26 biases the two halves 44a, 44b toward each other, causing their upper ends to pivot toward each other about the lower hinge in the absence of any restraint. The retention pin 24, when inserted, provides such a restraint against inward movement of the two halves 44a, 44b, and thus permits adjustment of the device 20 along the sutures 30a, 30b. When the retention pin 24 is removed, the coil spring 26 forces the two halves 44a, 44b radially together, thus reducing the size of the upper ends of the suture channels 36 to clamp inward against the sutures 30a, 30b. Once again the lower ends of the suture channels 36, and in particular the second apertures 42, remain unchanged. Because the inner walls of the two halves 44a, 44b are substantially parallel, and parallel to the coil spring 26 axis, the force on the sutures is radial, thus eliminating any possibility of slippage from axial forces.

At this stage it is important to understand that the coil spring 26 provides a relatively uniform inward biasing force to the two halves 44a, 44b, thus causing the halves to come together with the same force at the top as at the bottom. This helps better retain the sutures 30a, 30b since it maximizes the available surface area for gripping with a uniform force. The coil spring 26 thus provides an inward biasing force that is axially uniform, and thus could be replaced with any similar biasing member, such as a sleeve of elastic (e.g., silicone) material, or the like. Furthermore, though a coil spring 26 is advantageous for its relative economy and durability, the inward radial forces it supplies around the entire periphery of the locking clamp 22 could be replaced with a biasing member that simply applied compressive forces in the direction perpendicular to the plane between the two halves 44a, 44b. For instance, the locking clamp 22 itself could possess sufficient stiffness and be formed in such a way that removing the retention pin 24 causes the two halves 44a, 44b to come together and retain the sutures 30a, 30b without a surrounding spring. In such a configuration, a lock of sorts may also be provided to keep the two halves 44a, 44b together once they have clamped the sutures, and prevent outward creep. Alternatively, a spring with a more uni-directional action may be deployed around the locking clamp 22 to bias the two halves 44a, 44b together, such as a C-shaped clip or leaf spring, or the like. In short, the device 20 includes the two halves 44a, 44b and some sort of biasing force that causes them to come together upon removal of the retention pin 24.

In use, the technician assembles the device 20 with the retention pin 24 positioned in the retention pin channel 52 so as to force the two halves 44a, 44b apart against the radial compressive force of the coil spring 26. To facilitate this assembly, the lower end of the retention pin shaft 60 may be slightly tapered to facilitate introduction into the retention pin channel 52. The sutures 30a, 30b are threaded through the respective suture channels 36, preferably from the lower end through the larger second apertures 42 and upward through the device. As mentioned, the sutures 30a, 30b may be free ends of a suture loop that passes through soft tissue and through a heart valve sewing ring. Subsequently, the user advances the suture locking device 20 down the sutures 30a, 30b to the desired location, such as against the heart valve sewing ring. Adjustment of the sutures 30a, 30b through the device 20 results in a desirable tension in the sutures, at which point the user removes the retention pin 24 from the retention pin channel 52. The coil spring 26 instantaneously forces the two halves 44a, 44b together, pinching or clamping down on the sutures 30a, 30b. As will be described below, additional frictional features may be provided within the suture channels 36 to enhance the grip against the sutures. Finally, the remaining lengths of the sutures 30a, 30b extending above the device 20 are severed flush with the top face 40 of the circular flange 34. An exemplary tool for delivering and installing the suture locking device 20 is described below in reference to FIGS. 10 and 11.

The suture locking clamp 22 shown in FIGS. 6A and 6B features a vertical slot 46 and a lower horizontal hinge 48. An alternative locking clamp 22' shown in FIG. 7 includes essentially the same elements as described above such that similar numerals with a prime (') designation are utilized. The alternative locking clamp 22' has two halves 44a', 44b' separated across a vertical, diametric slot 46'. However, instead of a lower horizontal hinge, the locking clamp 22' has a vertical hinge 48' connecting the two halves 44a', 44b'. The locking clamp 22' desirably functions similarly to the earlier described clamp when combined with a retention pin and exterior coil spring, though the two halves 44a', 44b' pivot toward and away from one another about the vertical hinge 48'. Because of the different distances from the hinge 48', the suture channel 36' farther from the hinge experiences greater size changes than the channel closer to the hinge. Consequently, the relaxed size of the suture channel 36' farther from the hinge may be slightly greater than the size of the channel closer to the hinge so that they both apply the same amount of frictional clamping force on the sutures passing therethrough upon removal of the retention pin.

An alternative suture locking device 70 shown in FIG. 8 includes just an internal locking clamp 72 and an external coil spring 74 which cooperate to lock the position of the device along a pair of sutures 76a, 76b. In this embodiment, the coil spring 74 presses directly against the outside of the sutures 76a, 76b and pinches or clamps them against cutouts 78 formed in the outer surface of the locking clamp 72. To maintain the relative positions of the locking clamp 72 within the coil spring 74, the locking clamp may include outwardly projecting elements that engage the spaces between the coils of the spring. Furthermore, to adjust the device 70 along the sutures 76a, 76b, the free ends 80 of the coil spring 74 may be held in a position which forces open the spring so as to relax its inward compressive force against the sutures. At the appropriate position and tension within the sutures 76a, 76b, the restraining force on the free ends 80 is released such that the coil spring 74 tends toward its relaxed configuration, which produces a radially inward force against the sutures, forcing them into the cutouts 78. As will be explained below, additional frictional features may be provided in the cutouts 78.

Figure 9A:
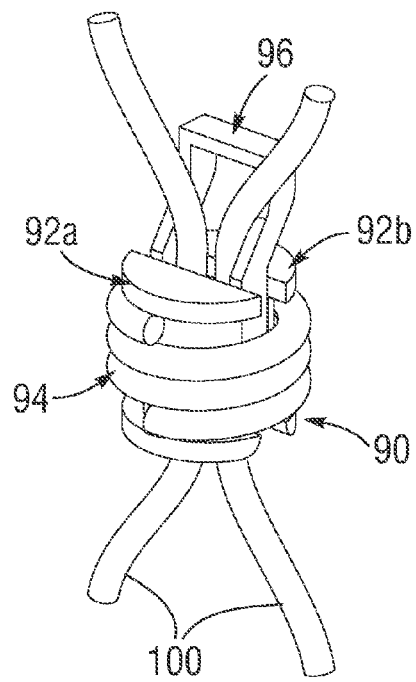
FIGS. 9A and 9B are perspective views of a still further alternative suture locking device shown, respectively, in assembled and locked modes.
Figure 9B:
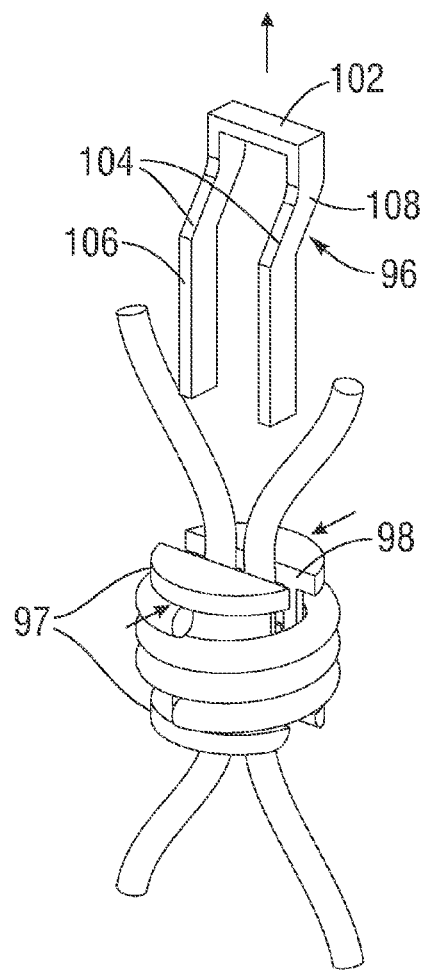

A still further alternative suture locking device 90 shown in FIGS. 9A and 9B includes a locking clamp having separate clamp halves 92a, 92b surrounded by an exterior coil spring 94 and having a two-pronged retention clip 96 therebetween. External flanges 97 on both ends of the clamp halves 92a, 92b maintain alignment of the halves with the coil spring 94. That is, the outward flanges 97 on opposite axial ends retain the coil spring 94 in position around the locking clamp. The inner walls of the clamp halves 92a, 92b are separated across a slot 98 through which pass two lengths of sutures 100. The coil spring 94 biases the two clamp halves 92a, 92b toward each other to reduce the size of the slot 98, but the presence of the retention clip 96 maintains an adequate slot width for adjustment of the device 90 along the sutures 100. Although not shown, the clamp halves 92a, 92b may feature cutouts for receiving the sutures 100 as in the embodiment of FIGS. 4-6.

Prior to use, a technician assembles the suture locking device 90 as seen in FIG. 9A by positioning the retention clip 96 between the clamp halves 92a, 92b and the sutures 100 through the slot 98. Desirably, the device 90 is pre-assembled by the manufacturer, i.e. the retention clip 96 and coil spring 94 would already be assembled with the clamp halves 92a, 92b. The surgeon or technician would only need to feed the sutures 100 between the clamp halves 92a, 92b at which point the device is ready to deploy using a tool such as described below. The retention clip 96 includes an upper bridge 102 joining two prongs 104. Each prong 104 includes a lower free end 106 and an upper angled portion 108 connected to the bridge 102. The angled portions 108 relocate the position of the bridge 102 out of direct alignment with the slot 98 such that the sutures 100 pass directly through the slot and may extend vertically upward. This offset also makes it easier to grab the bridge 102 by a deployment tool, as will be seen. The length of the lower free end 106 of each prong 104 is sufficient to maintain an even spacing between the inner walls of the clamp halves 92a, 92b against the inward bias of the coil spring 94.

In use, the suture locking device 90 in the configuration shown in FIG. 9A is advanced along the sutures 100 to the desired position. After proper adjustment of the tension in the sutures, the user removes the retention clip 96, as seen in FIG. 9b. The coil spring 94 has an inner coil diameter that forces the two clamp halves 92a, 92b toward each other so as to pinch or clamp the sutures 100 therebetween. Once again, additional frictional features may be provided on the inner walls of the clamp halves 92a, 92b, as will be described below with respect to FIGS. 12 and 13.

Figure 10:
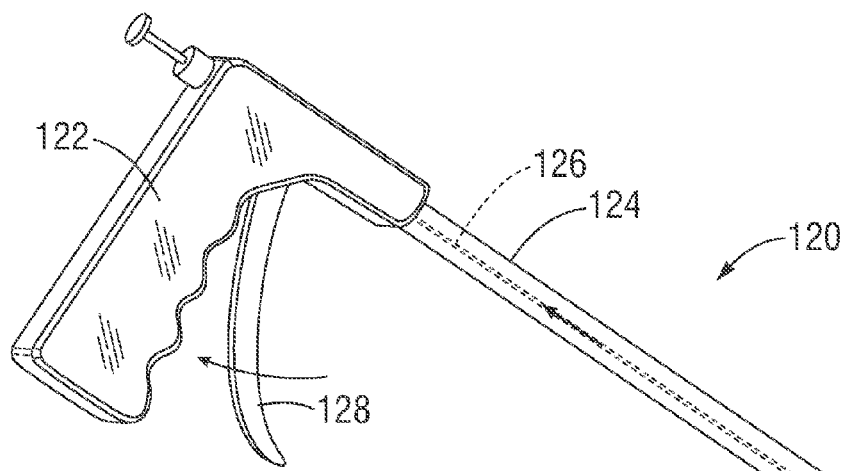
FIG. 10 is a perspective view of an exemplary tool for delivering and deploying the suture locking devices disclosed herein.
Figure 11:
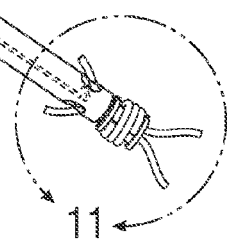
FIG. 11 is an enlarged perspective view of a distal end of the tool of FIG. 10 engaging the suture locking device of FIG. 9A.

Now with reference to FIGS. 10 and 11, an exemplary delivery and deployment tool 120 is shown and described. The illustrated deployment tool 120 primarily includes a proximal handle 122, an elongated tube 124, and an actuation rod 126. A trigger 128 causes longitudinal movement of the actuation rod 126 when depressed, through various mechanical means in the handle 122 that are well-known in the art and thus are not shown or described.

A distal end of the elongated tube 124 is shown enlarged in FIG. 11 engaging a suture locking device, such as the device 90 of FIGS. 9A-9B. More specifically, the distal end of the tube 124 contacts the upper flanges 97 of the device 90 such that the majority of the device projects distally from the tube while the retention clip 96 extends into the tube. A hook 130 on the distal end of the actuation rod 126 engages the bridge of the retention clip 96. The advantageous angled shape of the retention clip 96 facilitates this assembly. The sutures 100 extending through the device 90 pass outward through side apertures 132 formed in the tube 124. Although not shown, the sutures 100 may continue in a proximal direction along the tube 124 to a location outside of the surgical site. For example, if the tool 120 is used for installing the suture locking device 90 on the proximal side of a heart valve sewing ring, the sutures 100 represent two of a plurality of such sutures that are preinstalled at the annular site and pass through the heart valve sewing ring to a location outside the patient's body.

The proximal movement arrow 134 indicated in FIG. 11 shows displacement of the actuation rod 126 upon depression of the trigger 128. This action pulls the retention clip 96 from within the two halves 92a, 92b of the locking device 90, and enables the coil spring 94 to compress the two halves against the sutures 100 passing therethrough. Pulling the trigger 128 thus deploys the device 90. At this point the deployment tool 120 may be removed and the sutures 100 severed. Alternatively, edges of the side apertures 132 may be formed sharp so that rotation, axial movement, or other manipulation of the tool 120 causes the side apertures 132 to sever the sutures 100.

Figure 12:
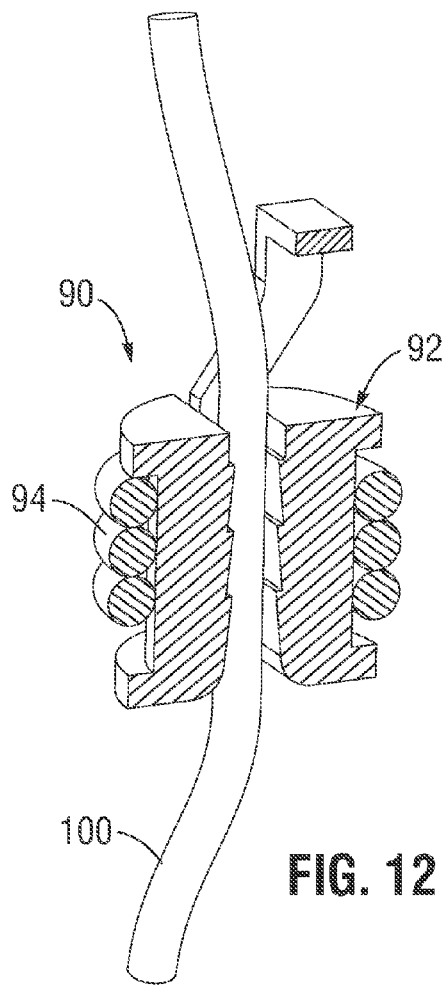
FIG. 12 is a longitudinal sectional view through the suture locking device of FIG. 8 illustrating enhanced frictional features therein.
Figure 13:
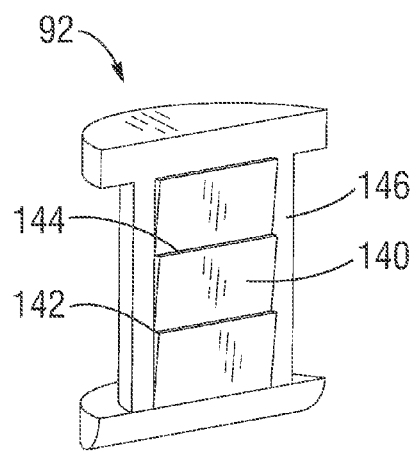
FIG. 13 is a view of an inner surface of one of the locking clamp halves of the device of FIG. 8.

FIG. 12 is a sectional view perpendicular to the slot 98 through the suture locking device 90 of FIGS. 9A-9B, while FIG. 13 illustrates an inside wall of one of the clamp halves 92. A series of angled ramps or teeth 140 are provided on the inner wall of the clamp half 92 to enhance friction between the device 90 and sutures 100 passing therethrough. In the illustrated embodiment, each of the angled teeth 140 slopes inward from a lower edge 142 to an upper edge 144. The lower edge 142 may lie flush with the borders 146 of the inner wall. When the two halves 92 clamp inward against the sutures 100, the angled teeth 140 help prevent relative sliding movement of the sutures downward through the device or, stated another way, help prevent loosening of the device from its clamped position. At the same time, the one-way gripping nature of the angled teeth 140 enable the surgeon to increase tension in the portion of the sutures 100 below the suture locking device 90 even after the device has been actuated. That is, the device 90 can be slid down the sutures 100 after actuation against the force of the coil spring 94 without too much difficulty. It should be understood that the angled teeth 140 are exemplary only, and representative of numerous configurations of enhanced friction within the clamp halves 92. For example, the inner wall may be roughened or provided with bumps, or series of horizontal ridges may be used.

Figure 14:
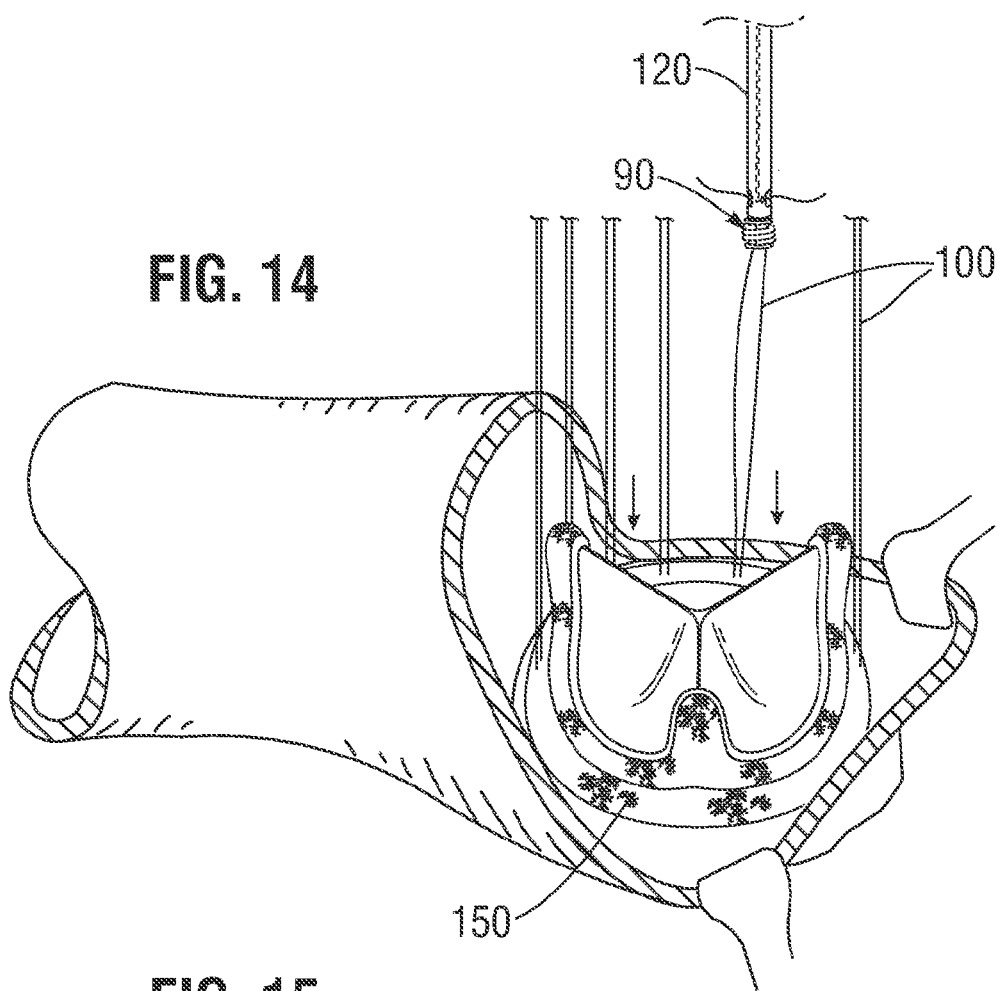
FIGS. 14 and 15 illustrate steps in an exemplary heart valve implantation procedure utilizing the suture locking devices described herein and a preferred implantation tool.
Figure 15:
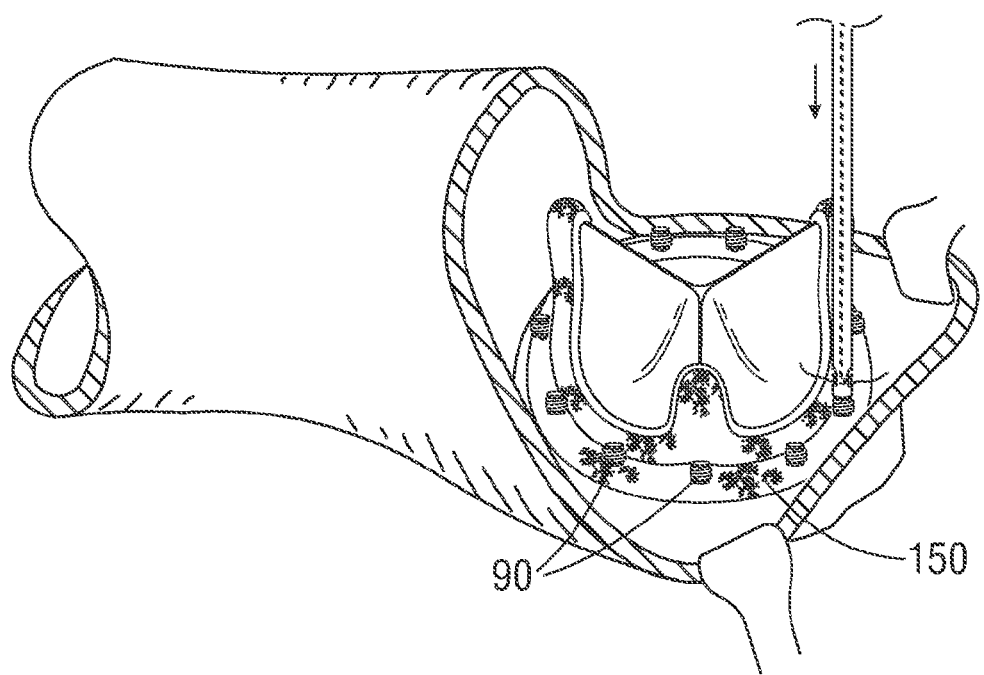

FIGS. 14 and 15 illustrates an exemplary procedure for securing a heart valve to a native annulus. Initially, the heart valve is shown in FIG. 14 after having been advanced along an array of sutures 100 that were preinstalled at the annulus. The sutures 100 pass upward through a sewing ring 150 of the heart valve in the same positions as they are installed at the annulus. Typically, a single suture passes down and up through the annulus to form a loop, and the suture pairs 100 shown represent a single loop. A deployment tool, such as the tool 120 shown and described above, is then used to advance a suture locking device, such as the device 90 of FIGS. 9A-9B, along a suture pair 100 until it reaches the proximal side of the sewing ring 150, as seen in FIG. 15. At this point, the free ends of the suture pair extending out of the implantation site may be pulled so as to appropriately adjust the tension in the sutures 100. Subsequently, actuation of the deployment tool 120 "activates" the locking device 90, such as by pulling free the retention clip 96, thus clamping the device onto the sutures 100. This secures the sewing ring 150 between the device 90 and the annulus. A plurality of the devices 90 are used around the heart valve as shown, typically between 8-16, and more preferably around 12. Alternatively, just three (3) of the locking devices 90 may be used for "hybrid" implants which feature an expandable anchoring structure, the three suture loops acting more as guides to orientation of the valve than anchors. Such a hybrid approach is seen in U.S. Ser. No. 13/167,639 to Pintor, et al., filed Jun. 23, 2011, the disclosure of which is expressly incorporated herein.

One particular advantage of the suture locking devices disclosed herein is their relatively small size, enabling installation of a plurality of the devices around a heart valve sewing ring without adding significant bulk. For example, both the height and outer diameter of the various devices disclosed herein are desirably about 2 mm or less, and may be as small as 1 mm (ie., between about 1-2 mm). The small size is enabled by the relatively large radial forces generated by the exterior coil springs as compared to the axial forces for the same spring. That is, for a given radial displacement of a single coil of a spring, the force in the radial direction is thousands of times higher than the force in the axial direction for the same axial displacement. Adding coils to the device adds to the radial force for a given radial displacement, but for a spring used axially, adding coils reduces the force. In other words, a spring with three coils produces three times the radial force compared to a single coil, whereas a spring with three coils used in the axial direction produces only ⅓ the axial force of a single coil in the axial direction. Because of the relatively large amount of force a spring can generate in the radial direction, a relatively small spring can be used to generate significant clamping forces, thus allowing for a very small device.

In a preferred embodiment, the various embodiments of the suture locking devices are made of biocompatible material, including a coil spring Stainless Steel, Cobalt-Chromium, Nitinol, or the like. For the clamp halves, any bio-compatible polymer (e.g., Nylon, Delrin, polypropylene) would be suitable, though metallic materials could also be used. The retention members (i.e., pin 26, clip 96) are desirably metallic to provide good compressive strength against the force of the coil spring. One specific example of a spring has an axial length of between 1-2 mm, an inner coil diameter of about 15.7 μm (0.040"), a wire diameter of about 5.9 μm (0.015"), and three coils. An exemplary spring constant is on the order of 53.6 g/mm (3 lbf/in). Of course, these parameters are examples only and a range of variations are possible. The miniature nature of the devices, however, render them highly useful for heart valve or annuloplasty ring implant suture anchors.

Further advantages of the devices disclosed herein are the speed and accessibility of the deployment procedure. Since the device is very small it can be delivered on the end of a relatively long and thin delivery shaft where a surgeon's finger may not fit or reach. It is estimated that it takes approximately 15-30 seconds to install each suture locking device, including feeding the sutures through the device, attaching it to the delivery tool 120, and activating the device. More particularly, the surgeon would first feed the sutures through one of the devices then through the end of the delivery tool. The retention element, such as the retention clip 96, is then engaged with the hook at the end of the actuator rod in the delivery tool, and a single squeeze of the trigger pulls the device flush with the distal end of the delivery tube. The surgeon then advances the device down the suture pair to the annulus, pulls the appropriate amount of tension on the sutures, then pulls the trigger again, which would retract the retainer out of the device, thereby activating it and allowing it to lock onto the sutures. The suture tails would also be cut at the end of the trigger stroke.

Moreover, in contrast with earlier suture locking devices, the present device relies on strictly radial inward forces of the coil spring to compress two clamp halves together, or to compress sutures against a clamp member. The clamp halves have parallel inner surfaces which are also parallel to the coil spring axis, so that purely radial clamping forces are generated. Many earlier devices rely on a wedging action between two surfaces, or between a wedge and surrounding surfaces, thus squeezing sutures between them. This utilizes an axial force of a spring or other retention member, potentially leading to loosening of the lock if one of the clamping members slips axially. Furthermore, in the process of locking the device, the relative sliding of the two retention surfaces may modify the suture tension. In the devices of the present application, the clamping members apply strictly radial forces, substantially instantaneously by removal of the retention pin or clip, which eliminates the risk of altering the suture tension. Furthermore, because the devices herein utilize springs to compress radially, much more clamping force is produced for a given size spring, which therefore allows the devices to be advantageously miniaturized compared to those which utilize an axial spring force. A locking device which uses an axial spring necessarily requires a minimum spring height, which may detrimentally interfere with certain implant procedures, such as heart valve replacements.

With reference now to FIGS. 16A-16H, a number of steps in an exemplary aortic heart valve implantation procedure illustrating the deployment of three suture locking devices, such as disclosed at 90 in FIGS. 9A and 9B, on a proximal side of a heart valve sewing ring. The procedure utilizes a plurality of automated delivery devices 220 that are shown in greater detail in FIGS. 17A and 17B.

FIGS. 16A-16H are sectional views through an isolated aortic annulus AA showing a portion of the adjacent left ventricle LV and ascending aorta AO with outwardly bulging sinus cavities. The aortic annulus AA is shown schematically isolated and it should be understood that various anatomical structures are not shown for clarity. The annulus AA includes a fibrous ring of tissue that projects inward from surrounding heart walls. The annulus AA defines an orifice between the ascending aorta AO and the left ventricle LV. Although not shown, native leaflets project inward at the annulus AA to form a one-way valve at the orifice. The leaflets may be removed prior to the procedure, or left in place as mentioned above. If the leaflets are removed, some of the calcified annulus may also be removed, such as with a rongeur. The ascending aorta AO commences at the annulus AA with three outward bulges or sinuses, two of which are centered at coronary ostia (openings) CO leading to coronary arteries CA. As will be seen below, it is important to orient the prosthetic valve so that its commissure posts are not aligned with and thus not blocking the coronary ostia CO.

The procedure illustrates the implant of a "hybrid" aortic prosthetic heart valve 222 that includes a valve member 224 attached during manufacture to a lower coupling stent 226. The valve member 224 represents a variety of different types of prosthetic heart valves, and as with many such valves includes a peripheral sewing ring 228 that rests on the ascending aorta AO side of the inwardly-directed shelf-like aortic annulus AA. The cloth-covered lower coupling stent 226 is delivered in a collapsed configuration, and is ultimately balloon-expanded outward against the native leaflets or, if the leaflets are excised, against the debrided aortic annulus AA as shown. Further details of the illustrated hybrid valve 222 as well as a similar aortic implant procedure are provided in U.S. Patent Publication No. 2012/0065729, filed Jun. 23, 2011, the contents of which are expressly incorporated herein.

Despite illustration of a particular procedure, it should be understood that the presently disclosed suture locking devices as well as instruments for deploying and securing the locking devices are useful in other contexts than implantation of a prosthetic aortic heart valve. For example, the same suture locking devices can be used to replace conventionally knotted sutures for prosthetic valve replacements at other native annuluses. Likewise, the suture locking devices can be used to secure annuloplasty rings to any of the native annuluses. More broadly, the suture locking devices could be used in any surgical environment in which sutures are used to secure objects or tissue in place and typically require knotting. The suture locking devices replace the function of the suture knots, and since they are more quickly deployed they reduce the respective procedure times.

Figure 16B:
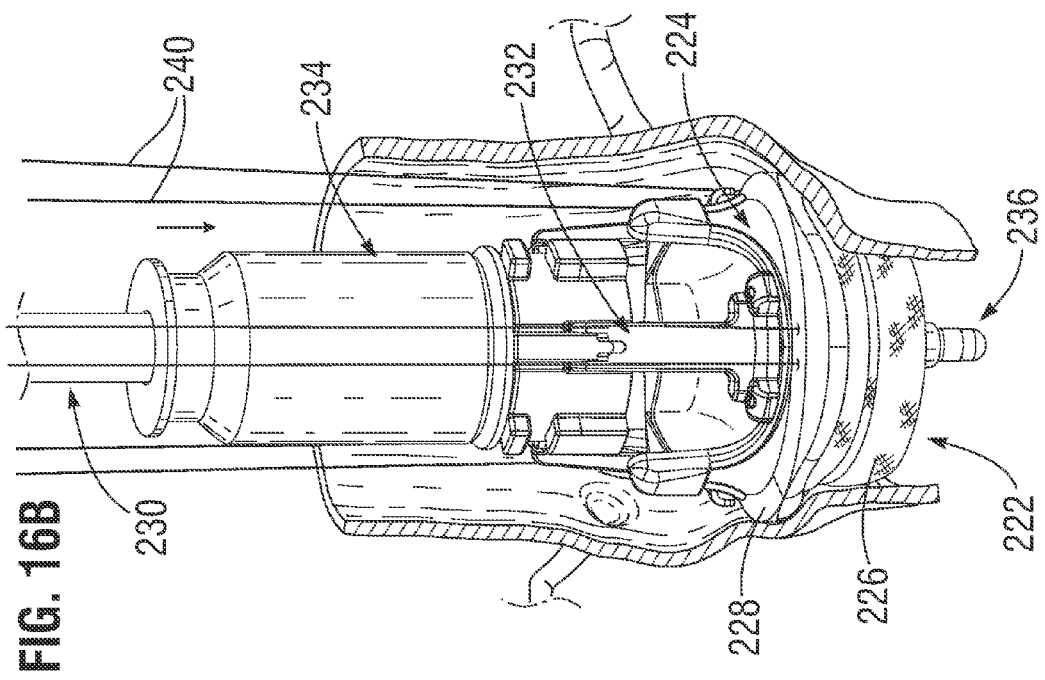
Figure 16A:
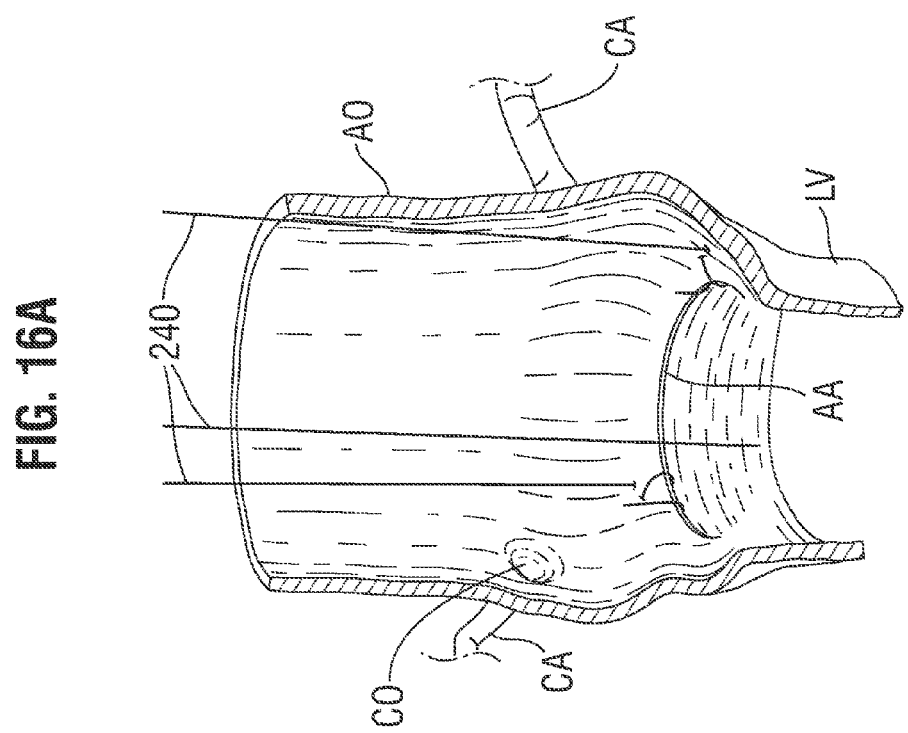

FIG. 16A shows a preliminary step in preparing an aortic annulus AA for receiving the heart valve including installation of guide sutures 240. The surgeon attaches the guide sutures 240 at three evenly spaced locations around the aortic annulus AA. In the illustrated embodiment, the guide sutures 240 attach to locations below or corresponding to the coronary ostia CO (that is, two guide sutures are aligned with the ostia, and the third centered below the non-coronary sinus). The guide sutures 240 are shown looped twice through the annulus AA from the outflow or ascending aorta side to the inflow or ventricular side. Of course, other suturing methods or pledgets may be used depending on surgeon preference.

FIG. 16B shows the guide sutures 240 having been secured so that each extends in pairs of free lengths from the annulus AA and out of the operating site. The hybrid prosthetic heart valve 222 mounts on a distal section of a delivery system 230 and the surgeon advances the valve into position within the aortic annulus AA along the guide sutures 240. That is, the surgeon threads the three pairs of guide sutures 240 through evenly spaced locations around the sewing ring 228. If the guide sutures 240, as illustrated, anchor to the annulus AA below the aortic sinuses, they thread through the ring 228 mid-way between the valve commissure posts. Thus, the guide sutures 240 pass through the sewing ring 228 at the cusps of the valve and are less likely to become tangled with the valve commissure posts. Furthermore, the exemplary sewing ring 228 has an undulating inflow side such that the cusp locations are axially thicker than the commissure locations, which provides more material for securing the guide sutures 240.

As seen in FIG. 16B, the valve delivery system 230 includes a heart valve holder 232 which preferably includes three legs that extend downward to the valve cusps. A tubular sleeve 234 connects to an upper hub of the valve holder 232, and a balloon dilatation catheter extends through the assembly; a distal tip 236 of which is shown. As explained better in U.S. Patent Publication No. 2012/0065729, mentioned above, the valve delivery system 230 advances the prosthetic heart valve 222 down the pairs of guide sutures and into place against the aortic annulus AA, at which time the balloon of the balloon dilatation catheter expands to outwardly expand the cloth-covered anchoring skirt 226 against the subvalvular wall.

FIG. 16C shows the hybrid heart valve 222 in phantom (for clarity) in a desired implant position. One of a plurality of automated delivery devices 220 used to install suture locking devices of the present application is shown schematically adjacent the delivery system 230. A suture locking device 250 such as one of the devices described previously is held at a distal end of a hollow tube 251 of the delivery device 220. One pair of the guide sutures 240 is shown being threaded through a capture loop 252 on the distal end of the delivery device 220 by forceps 254. FIG. 16D shows the pair of guide sutures 240 being threaded through the suture locking device 250 and through the hollow tube 251 by pulling on a suture snare having an upper loop 256 connected to the capture loop 252. Ultimately, the guide sutures 240 are pulled proximally through the entire delivery device 220 and held outside the implantation site. FIG. 16E then shows advancement of the delivery devices 220 toward the hybrid heart valve 222 until the suture locking devices 250 abut the sewing ring 228 thereon.

In FIG. 16F, forceps 254 are used to bend outward upper ends of the hollow tubes 251 of the delivery devices 220 to improve access to the heart valve 222 and implant site. The delivery tubes may be made of an easily bendable or malleable material, such as aluminum, or could be a series of linked elements that provide axial stiffness yet lateral flexibility. FIG. 16G shows expansion of the cloth-covered anchoring skirt 226 on the hybrid heart valve 220 against the subvalvular wall and subsequent removal of the delivery system 230. The surgeon actuates the delivery devices 220 to clamp the suture locking devices 250 onto the guide sutures 240, as will be explained below. Finally, FIG. 16H shows detachment of the delivery devices 220 from the suture locking devices 250 and removal of the tubes from the implantation site.

FIGS. 17A and 17B show an exemplary automated delivery device 220 used in the procedure illustrated in FIGS. 16A-16H in both sectional and perspective views. As mentioned, the suture locking device 250 is held on the distal end of the hollow tube 251, preferably by an interference between a small nib 260 on an upper end of the locking device 250 and an inner lumen of the hollow tube 251. Aside from this engagement with the delivery device 220, the locking device 250 may be identical to the suture locking device 90 shown in FIGS. 9A and 9B, and includes a locking clamp having separate clamp halves 264 surrounded by an exterior coil spring 262 and having a two-pronged retention clip 266 therebetween.

As described above, the suture snare has the upper loop 256 which connects to the capture loop 252 via one or more filaments 270 that extend through the hollow tube 251 the entire length of the device 220. The capture loop 252 may be held open by a removable silicone ring 272 that has an exterior channel so that it does not slip free of the capture loop. It will be understood that the entire suture snare including the silicone ring 272 can be easily pulled upward through the middle of the locking device 250 and delivery device 220. The capture loop 252, filaments 270 and upper loop 256 may be made of a flexible and strong material, such as suture thread.

A locking device release button 280 is located at the upper end of the delivery device 220 and attaches to a pair of filaments 282 that extend downward either through or along the outside of the hollow tube 251. The illustrated bottom, the filaments 282 extends along the outside of the tube 251 and pass inward through a pair of side apertures 284 at the lower end of the tube. The two filaments 282 are then secured to the retention clip 266 held in the locking device 250. Tension in the filaments 282 can pull the retention clip 266 upward, thus actuating the locking device 250. It is important to note that the filaments 282 perform an equivalent function as the actuation rod 126 seen in FIGS. 10 and 11, and the two configurations may be commonly termed elongated tension members.

With reference back to the procedure step of FIGS. 16C-16E, the locking device release button 280 is shown separated from an upper end of the hollow tube 251. This permits passage of the suture snare and guide sutures 240. As seen in FIG. 16F, the release button 280 may be temporarily secured on the upper end of the hollow tube 251 for part of the procedure to reduce clutter at the operating site. After removal of the valve delivery system 230, as in FIG. 16G, the surgeon pulls the release button 280 which tensions the filaments 282 and pulls the retention clip 266 upward, thus actuating the suture locking device 250. The same procedure is carried out for as many of the delivery device 220/locking device 250 combinations there are (in the illustrated embodiment, just three). Ultimately, the hybrid heart valve 220 is secured in place at the annulus by the locking devices 250 as well as the outwardly expanded anchoring skirt 226. After each locking device 250 is actuated, the associated delivery device 220 can simply be removed. Desirably, removal of the retention clip 266 allows the two clamp halves 264 (see FIG. 17B) to come together a little to relieve the interference with the tube 251.

FIGS. 18 and 19 are longitudinal sectional views of alternative mechanisms for temporarily tensioning sutures to the automated delivery tubes disclosed herein. In FIG. 18, a tensioning assembly 290 includes an annular cap 292 affixed to the proximal end of the delivery device 220 on which a lever arm 294 pivots. The lever arm 294 has teeth or a similar expedient at a distal end that engages similar teeth 296 on an inner wall of the annular cap 292, the lever arm being biased by a spring 298 toward the teeth 296. A user can feed the guide suture 240 between the engaging teeth 296 while pulling back the lever arm 294, and then release the lever arm 294 to grab the suture with the teeth. This permits easy adjustment of the tension in the guide suture 240 and then fees up the surgeon to concentrate on the other aspects of valve implant before the locking device 250 is actuated.

Likewise, FIG. 19 shows a tensioning assembly 300 on the proximal end of the delivery device 220 comprising a rotatable cleat 302. The surgeon wraps the guide suture 240 around the cleat 302 until frictional forces hold it in place, and then can tighten or loosen the tension by rotating the cleat 302. Of course, other such arrangements are contemplated.

The present application also contemplates a "side-entry" suture locking device 350, as shown in FIGS. 20-25. As before, the device 350 provides a suture locking retainer which eliminates the need for tying knots in surgical sutures. The suture locking device 350 includes a bifurcated locking clamp 352 having an axial hinge 354, like in FIG. 7. The locking clamp 352 can be manufactured from plastic by molding. The locking clamp 352 has two substantially identical halves 356a, 356b separated by a variable-sized slot 358 and biased together by at least one exterior "C" clip 360. The axial hinge 354 is desirably a "living hinge" formed in the molded part along one side so that the halves 356a, 356b can pivot apart to vary the size of the slot 358 and form an opening on the side opposite from the hinge in which sutures can be inserted. Alternatively, a true hinge may be provided between the two halves 356. One or more of the C-clips 360 are placed around the clamp and sized such that they apply a force which acts to close the clamp 352 and close or eliminate the slot 358, thus clamping onto sutures that pass through the slot. The C-clip(s) 360 thus provide the biasing member positioned on the outside of the locking clamp 352 having a relaxed size that, in the absence of any other object in the slot 358, urges the inner surfaces of the clamp halves 356 together such that the slot has a width smaller than the suture thickness. In an alternative configuration, a section of tube with a slit (forming a "C" in cross section) could replace the array of "C" clips. Indeed, the term, "biasing member" should be understood to refer to one or more elements as described herein.

As with the earlier embodiments, an overall exemplary size of the device can be 2 mm in height and diameter, or smaller. The initial design shown here is based on 2-0 sutures, which are commonly used in valve replacement procedures. Furthermore, the dimensions and parameters for materials described above for the earlier embodiments also apply to the locking device 350 of FIGS. 20-25.

As seen in FIG. 21, each half 356 includes a semi-cylindrical middle recess 362 between two outwardly-projecting end flanges 364. When the two halves 356 are brought together, they define a spool shape. As seen in FIGS. 20A, 20B, the C-clips 360 are received in the recess 362 with their open ends 366 flanking the variable-sized slot 358 and directly opposed to the hinge 354. The end flanges 364 hold the C-clips 360 in place.

The C-Clips 360 would most likely be formed from stainless steel wire, although other materials should not be excluded. For the exemplary embodiment shown, the C-clips 360 are formed from 0.008" diameter wire and have an outside diameter of 0.079" (2 mm). The illustrated embodiment incorporates 5 C-clips 360, though additional C-clips 360 could be added to increase the clamping force. Additionally, the clamping force can be increased significantly by small increases in the wire diameter of the C-clips 360. The bending stiffness of a circular wire is proportional to the $4^{th}$ power of its diameter, and so increasing the wire diameter from only 0.008" to 0.010" increases the clamping force by a factor of 2.4, while an increase to 0.012" would result in a 5-fold increase in clamping force. Thus by changing the number of C-Clips and their wire diameters, large changes in the clamping force can be realized with minimal impact on the device diameter and small changes in device height.

FIGS. 24A-24D illustrate a sequence of operation of the side entry suture locking device 350. First, the assembled locking device 350 includes the aforementioned components as well as a retention pin 370. Prior to use, the two halves 356a, 356b are forced apart so that the retention pin 370 may be inserted into a retention pin channel 372, as seen best in FIG. 22. The retention pin channel 372 is defined between the axial hinge 354 and an axially-oriented retainer rib 374 formed on one or both halves 356 and extending into the slot 358. Release of the two halves 356 permits the C-clips 360 to force the two halves to pivot toward one another and clamp onto the retention pin 370. Preferably, the device 350 is pre-assembled by the manufacturer, i.e. the retention pin 370 and C-clips 360 are pre-assembled with the clamp halves 356a, 356b. The presence of the retention pin 370 holds open the two halves 356a, 356b so that the slot 358 widens into the opening opposite the hinge 354 into which one or more sutures 380 can be inserted.

As a first step in the process of deployment, the surgeon laterally displaces one of the suture locking devices 350 toward one or more sutures 380, as seen in FIG. 24A. As mentioned, the slot 358 defines an opening into which the sutures 380 are received. As seen in FIG. 24B, the surgeon then tensions the sutures 380 while the suture locking device 350 is held stationary or pressed (seated) against a stationary substrate, such as the proximal face of a prosthetic heart valve sewing ring or annuloplasty ring. In FIG. 24C, the retention pin 370 is removed, thus allowing the C-clips 360 to force closed the opposite halves 356a, 356b of the clamp 352, thus clamping the suture(s) 380 therebetween, as seen in FIG. 24D.

With reference back to FIG. 22, the inner faces of one or preferably both of the device halves 356a, 356b include a plurality of grip members 382 that help prevent relative movement between the deployed device 350 and the sutures 380. More particularly, the grip members 382 prevent relative longitudinal movement between the device 350 and sutures 380 in only one direction. For example, the grip members 382 are formed as wedges with a ramp angled in one axial direction, in the illustrated embodiment the wedges are angled upward. Due to their orientation, and after the device 350 has been deployed about sutures 380, the sutures would be prevented from moving relatively downward, but could be pulled through upward. Stated another way, the device 350 could be slid downward on the sutures, but not upward. This configuration enables the surgeon to increase the tension on the sutures 380 once the locking device 350 is closed, but loosening of the sutures would be inhibited. Desirably, both inner faces of the device halves 356a, 356b include an axial bar 384 that helps retain the sutures 380 within the slot 358. As seen in FIG. 24D, the bars 34 extends sufficiently inward toward each other so as to close and present a barrier to lateral escape of the sutures 380.

FIG. 25 illustrates how the suture(s) 380 can be tensioned further after deployment of the device 350. It will be noted that only one suture 380 is shown in this view to emphasize that one or more can be secured by the device 350. The individual grip members 382 could be axially offset on the two halves 356 to enhance their frictional hold on the suture(s) 380. In other words, deploying the device 350 creates a serpentine path for the suture(s) 380 between the alternating grip members 382. The cross-section of the slot 358 shows the offset suture grips 382, which thus act as a "one way" ratchet that allows for further tensioning of the suture(s) after deployment of the device, but resist loosening of the sutures.

FIG. 25 also shows an alternative clip/suture arrangement where one end 390 of the suture 380 is fixed to the locking clamp 352, such as by embedding a bead 392 or other such enlargement. That is, one end 390 of the suture pre-attaches to the one of the device halves 356a, 356b, which could be done by insert molding the end as shown, or simply tying one end of the suture to the device. This means that the device 350 only clamps onto one suture 380, which might be easier to align in the clip and easier to consistently capture. This arrangement would be preferred for robotic surgery where both ends of the suture are typically not run out of the incision. In a typical cardiac repair or replacement procedure, the free end 380 of the suture having a suture needle attached the is passed down through the implant and the annulus, then back up through the implant in about the same location and pulled taut so as to pull the locking device 350 against the implant. The free end 380 is inserted through the clamp slot 358 and tensioned, whereupon the retention pin 370 is removed to lock the device 350 onto the suture. In addition to the side entry device 350, this arrangement could also be utilized with the earlier embodiments where the sutures pass through from end-to-end.

Figure 26A:
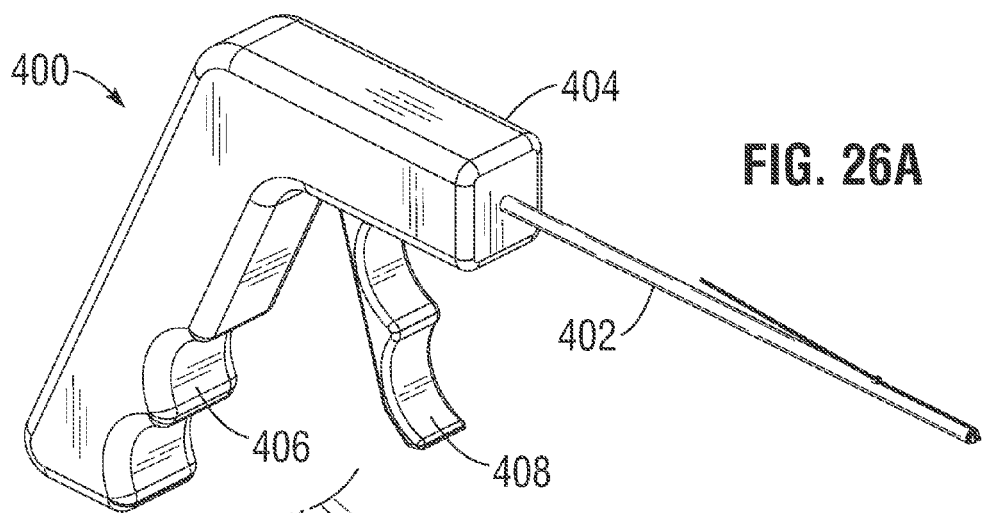
FIGS. 26A-26C are perspective views of an exemplary delivery system for the side entry suture locking devices described herein.
Figure 26B:
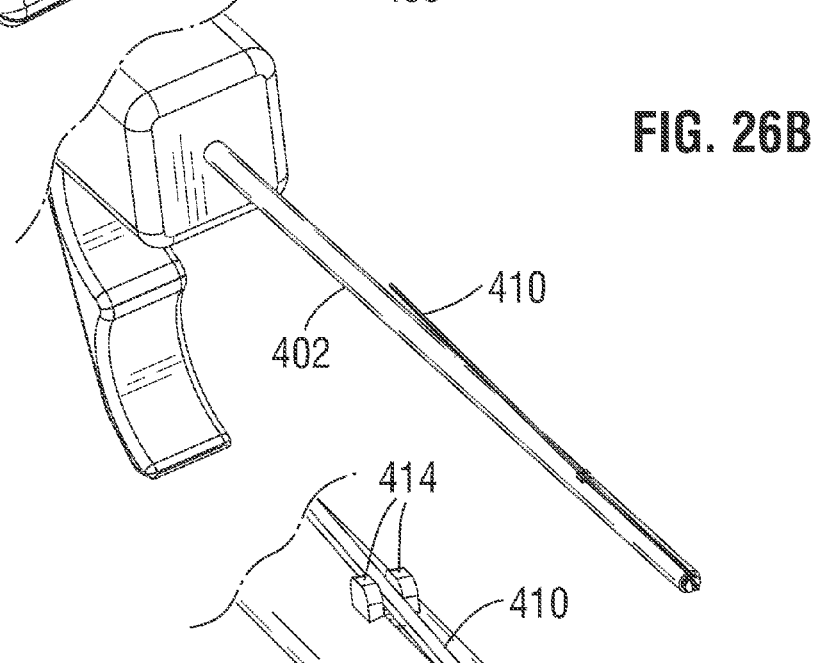
Figure 26C:
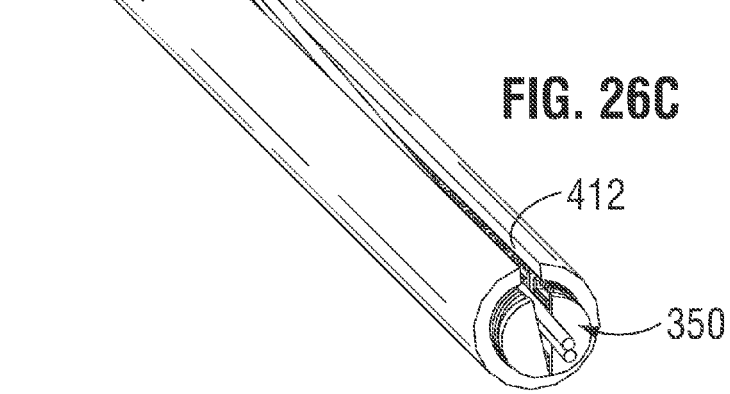

FIGS. 26A-26C illustrate an exemplary delivery system 400 for the side entry suture locking devices 350 described herein. In the illustrated embodiment, the system 400 is shown as a pistol-like device with a long, malleable shaft 402 extending from a proximal handle 404 having a grip 406 and an actuation trigger 408. Of course, the system can be modified so that the handle 404 is generally aligned along the axis of the shaft 402, with a slider as an actuator, or any other such configuration.

As seen in the detailed view of the distal end of the tubular shaft 402 in FIG. 26C, a pair of sutures 410 is tensioned at a shallow angle with respect to the shaft so as to enter a longitudinal channel 412 on one side of the shaft and into the slot formed in one of the side entry suture locking devices 350. A pair of guides 414 project outward from the shaft 402 at the proximal termination of the channel 412 to help maintain alignment of the sutures 410 into the channel. An inner lumen of the shaft 402 has a diameter sufficient to receive a plurality of pre-loaded suture locking devices 350 in their undeployed configuration. A series of the locking devices 350 are stacked axially against each other within the tubular shaft 402 with their slots oriented toward the shaft channel 412.

FIG. 27 is an exploded perspective view of components of the side entry suture locking device delivery system 400 which includes the aforementioned exterior shaft 402, a series of the stacked locking devices 350, an elongated retention pin or cable 420, and an inner pusher tube 422 that slides within the lumen of the shaft 402. As seen in the sectional views of FIGS. 28A and 28B, the retention cable 420 extends through a lumen within the pusher tube 422 to the distal end of the shaft 402 and is positioned within the distalmost suture locking device 350. The retention cable 420 performs the same function as the aforementioned retention pin 370 described above with reference to a single locking device 350. That is, the common retention cable 420 extends through the series of locking devices 350, maintaining each of them in its undeployed configuration. At the same time, the retention cable 420 holds the series of locking devices 350 within the system 400. To enhance release of each suture locking device 350, a small raised area 424 (see FIG. 29D) may be provided on one end of each half of the device to separate the devices from each other, as seen in FIG. 28B. These raised areas 424 of the proximalmost device 350 are received within a stepped bore 426 in the distal end of the pusher tube 422.

In a preferred embodiment, the retention cable 420 and pusher tube 422 are displaced axially by a movement mechanism (not shown) within the proximal handle 404. As will be described in more detail below, the movement mechanism is configured to retract the cable 420 proximally relative to the tube 422, and advance the cable 420 and tube 422 together distally within the shaft 402. For example, depression of the trigger 408 retracts the retention cable 420 within the pusher tube 422, and release of the trigger urges both the retention cable 420 and pusher tube 422 distally within the shaft 402. In each trigger pull and release, the retention cable 420 retracts within the pusher tube 422 a distance equivalent to the axial height of one of the suture locking devices 350, and the cable 420 and tube 422 advance the same distance.

With reference to FIG. 28B, one of the suture locking devices 350 is shown released from the series within the shaft 402. In a preferred embodiment, the distalmost locking device 350 while still being retained on the retention cable 420 is located beyond the end of the shaft 402, although the locking device could also be partly or wholly within the shaft. In this position, the retention cable 420 extends substantially all the way through the distalmost locking device 350, such as shown with the next locking device in FIG. 28B. Depression of the trigger 408 then pulls/retracts the retention cable 420 a distance equal to the height of the locking device 350, thus deploying the distalmost locking device, or in other words permitting the C-clips 360 to close the slot 358 around the sutures 410. Placing the sutures 410 through the channel 412 and into the slot 350 of the distalmost locking device 350 ensures that the locking device will clamp onto the sutures when it is expelled. At this point, the surgeon releases the trigger 408 which causes axial advancement of both the tension cable 420 and pusher tube 422, thus moving the stack of locking devices 350 and positioning the distalmost device either outside of the shaft 402 or in a location where it can be easily released therefrom.

In an alternative configuration, the retention cable 426 fixedly attaches to the proximal handle 404 and thus remains with its distal end approximately even with the distal end of the shaft 402, or slightly recessed therein. Only the pusher tube 422 attaches to a movement mechanism (not shown) within the proximal handle 404. Actuation of the trigger 408 causes distal movement of the pusher tube 422 within the shaft 402. For example, actuation of the trigger 408 translates into distal movement of the pusher tube 422 equivalent to the axial height of one of the suture locking devices 350. That is, pulling the trigger 408 causes the pusher tube 422 to push one of the pre-loaded locking devices 350 out of the end of the shaft 402. Of course, once the suture locking device 350 is expelled from the end of the shaft 402, it also releases from the retention cable 420, thus causing its deployment. This configuration is slightly less desirable than the one described above because during deployment the suture locking devices 350 move relative to the sutures 410 which are stationary. Nevertheless, the point is made that there are a number of ways to expel one suture locking device 350 at a time from the distal end of the shaft 402 while the same time retracting the retention cable 420 and clamping the locking device onto the sutures 410.

It is important to understand that components of the various deployment tools for the suture locking devices described herein could be modified and exchanged. That is, the retention cable 420 for the delivery system 400 could be replaced by the actuation rod 126 of the deployment tool 120 (FIG. 11) or the filaments 282 of the delivery device 220 (FIG. 17B), and vice versa. In particular, each of the several suture locking devices (20, 70, 90, 350) disclosed herein includes a bifurcated locking clamp defining a variable-sized slot which is biased toward a closed position. A retention member, such as the retention cable 420, maintains the slot open so that one or more sutures can be inserted into the slot, and when the retention member is removed the slot closes onto the suture(s). It should be understood that removing the retention member can be accomplished in various ways, and a preferred embodiment is an elongated tension member extending along the deployment tool and actuated from a proximal end. In the delivery system 400 the retention cable 420 defines the elongated tension member and the retention member within the locking clamp 352, while in the earlier-described single-device embodiments the tension members and retention members are separate elements. However, those of skill in the art will understand that the delivery system 400 could be modified to be a single-device tool and have separate tension members and retention members.

Preferably, the outer shaft 402 is malleable or bendable into various shapes which significantly enhances the ability of a surgeon to correctly position the distal end of the system 400 as it advances toward the target location. For example, access passageways into the heart during a surgical procedure are often somewhat confined, and may not provide a linear approach to the annulus. Accordingly, the surgeon bends the shaft 402 to suit the particular surgery. Various materials and constructions may be utilized for the malleable shaft 402. For example, a plurality of Loc-Line connectors could be used which provide axial rigidity with bending flexibility. Another example is a plastic tube having a metal coil embedded therein to prevent kinking. In a preferred embodiment, an aluminum tube having a chromate (e.g., Iridite) coating is used. Aluminum is particularly well-suited for forming small tubes that can be bent without kinking, but should be coated with Iridite or the like to prevent deterioration in and reaction with the body.

Furthermore, both the retention cable 420 and the pusher tube 422 are made of flexible materials to complement the malleability of the shaft 402. For example, the retention cable 420 could be a braided wire rope or solid flexible wire. The pusher tube 422 could be made of a flexible polymer, though other materials are contemplated.

Figure 29A:
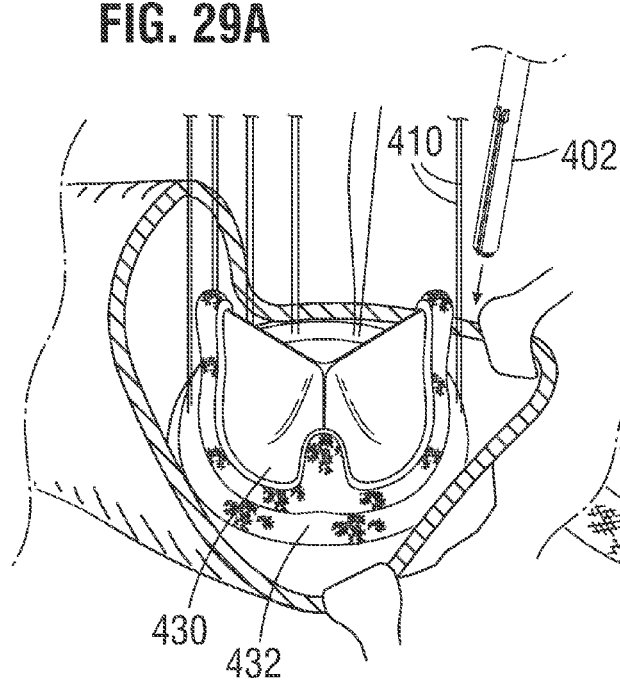
FIGS. 29A-29D are schematic views showing steps in use of the delivery system to deploy one of the side entry suture locking devices during a prosthetic heart valve implantation procedure.
Figure 29B:
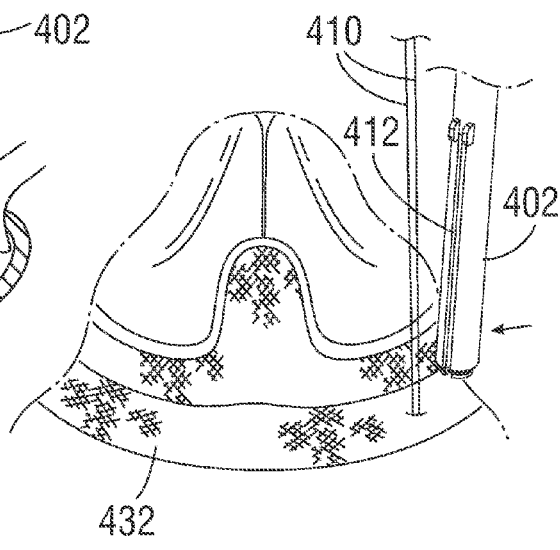
Figure 29C:
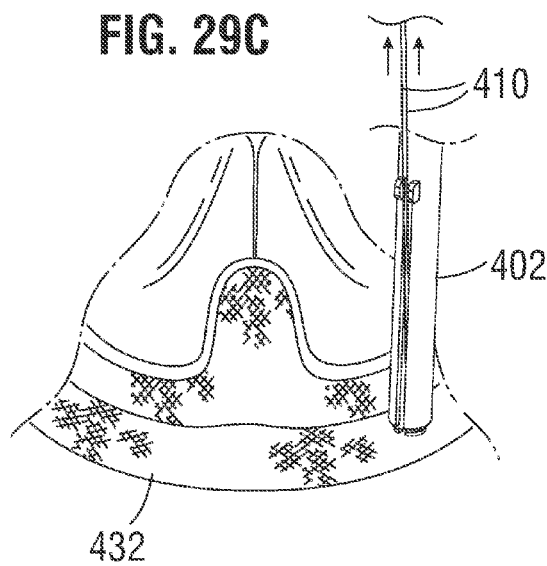
Figure 29D:
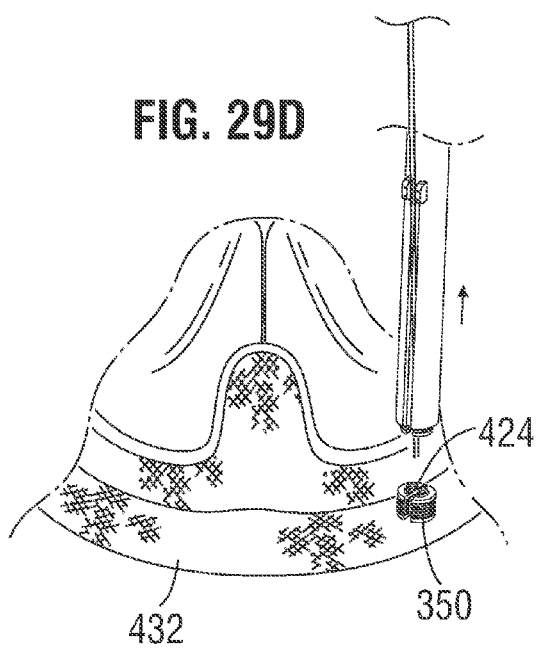

FIGS. 29A-29D show several steps in use of the delivery system 400 to deploy one of the side entry suture locking devices 350 during a prosthetic heart valve implantation procedure. As was described with respect to FIGS. 14 and 15 above, the heart valve 430 is shown in FIG. 29A after having been advanced along an array of sutures 410 that were preinstalled at the annulus. The sutures 410 pass upward through a sewing ring 432 of the heart valve in the same positions as they are installed at the annulus. Typically, a single suture 410 passes down and up through the annulus to form a loop, and the suture pairs shown represent a single loop. The distal end of the delivery system 400 is shown advancing toward the annulus and heart valve 430 seated thereon.

FIG. 29B is an enlarged view showing the distal end of the system 400 just prior to contact with the heart valve sewing ring 432. The pair of sutures 410 that will be secured are routed into the channel 412 on one side of the shaft 402. The shaft 402 is the advanced until its end or the distalmost locking device 350 contacts the sewing ring, as in FIG. 29C. The suture guides 414 projecting outward from the shaft 402 help maintain the position of the sutures 410 as the surgeon pulls tension on the sutures before activating the lock, as indicated in FIG. 29C.

At this point, the surgeon activates the movement mechanism within the proximal handle 404 by pulling the trigger 408 which deploys the distal-most locking device 350 to clench the sutures 410, as was depicted in the detail of FIG. 28B. Momentarily, the trigger 408 remains in the fully depressed position, and the system 400 may be pulled free of the pair of sutures 400. The sutures 410 are then severed close to the device 350. For this purpose, a knife edge (not shown) could be incorporated into the end of the shaft 402 to facilitate cutting the suture tails after each locking device 350 is deployed.

The next locking device 350 is then positioned for deployment by releasing the trigger 408 which, as described above, simultaneously advances the tension cable 420 and pusher tube 422 by a length equal to one locking device. The surgeon can then reposition the distal end of the shaft 402 around the heart valve sewing ring 432 toward the next pair of sutures 410 to be secured. Because of the series of pre-loaded devices 350 all of the pairs of sutures 410 can be secured and the valve 430 anchored to the annulus in a very short time. This greatly simplifies the use of the system and saves valuable OR time as well as on-pump time when used in open heart procedures. A less complicated and more inexpensive version could be made with a single locking device 350 per delivery system, which could be more practical when only 3 or so devices needed to be used for a particular procedure, as opposed to 12-20 for a conventional surgical valve replacement.

The suture locking devices and deployment systems disclosed herein could be used for eliminating knot-tying in surgical valve replacement, surgical valve repair (i.e., annuloplasty), or in general wherever sutures are used in surgery. They could be used with standard surgical valves where there are 10 or more pairs of sutures (e.g., 12-20), or with the EDWARDS INTUITY valve system from Edwards Lifesciences of Irvine, Calif. to eliminate the need for knot tying of three pairs of sutures located equidistantly around the sewing ring. Another possibility would be to incorporate suture locking devices within a pre-positioned tube and replace the proposed snares/tubes used for anchoring the EDWARDS INTUITY valve system during deployment. Likewise, the devices could be pre-attached to the sewing ring of an aortic or mitral valve. For instance, the sewing ring could incorporate radial slits adjacent to embedded suture locking devices such that after the sutures were placed in the annulus they would simply be guided through the slits and into the slots of the devices. Each suture pair could then be tensioned and the lock engaged.

Another advantage of the suture locking devices disclosed herein is there low cost of manufacture. For example, the side entry locking devices 350 comprise a molded component and several formed wire C-Clips. Even if 10 or more of the devices are required for a procedure, the cost is much less than existing systems.

While embodiments and applications of this invention have been shown and described, it would be apparent to those skilled in the art that many more modifications are possible without departing from the inventive concepts herein, and it is to be understood that the words which have been used are words of description and not of limitation. Therefore, changes may be made within the appended claims without departing from the true scope of the invention.

What is claimed is:

1. A method for anchoring a cardiac implant to a native valve annulus, the implant having been advanced to the native valve annulus down a plurality of loops of suture that are preinstalled at the native valve annulus, the sutures having a thickness, the method comprising:

threading two free ends of each of the suture loops through one of a plurality of suture locking devices, each device having a bifurcated locking clamp including a pair of substantially similar clamp halves each having an exterior surface and an inner surface facing the inner surface of the other clamp half, the clamp halves being fixed axially with respect to one another while being connected for movement toward or away from each other to form a variable sized slot having a width between the inner surfaces through which the free ends extend, each device further including a biasing member that, in the absence of any other object in the slot, urges the inner surfaces of the clamp halves together such that the slot has a width smaller than the suture thickness, each device further having a retention member positioned between the clamp halves against the force of the biasing member with a thickness that maintains the slot width large enough to permit passage of the suture free ends therethrough;

advancing the suture locking devices down the free ends of the suture loops until the locking devices contact the implant;

adjusting tension in the free ends of the suture loop passing through each locking device;

proximally pulling the retention member from between the clamp halves of each locking device, thus enabling the biasing member to force the clamp halves toward and clamp onto the free ends of the corresponding suture loop; and severing the free ends of the suture loop flush with a top face of the corresponding device.

2. The method of claim 1, further including:

providing an elongated delivery tool having a proximal end and distal delivery tube, the tool further including an elongated tension member that extends along the delivery tube and that may be displaced axially from the proximal end;

assembling each suture locking device with a distal end of the delivery tube by engaging a distal end of the elongated tension member with the retention member of that locking device;

advancing each suture locking device on the distal end of the delivery tube down the free ends of the suture loop until the locking device contacts the implant;

displacing the elongated tension member so as to proximally pull the retention member from between the clamp halves of the device on the distal end of the delivery tube, thus enabling the corresponding biasing member to force the clamp halves toward and clamp onto the free ends of the corresponding suture loop.

3. The method of claim 2, wherein the retention member comprises a bifurcated retention clip with a connecting bridge, and the elongated tension member has a hook on the distal end thereof that engages the bridge of the retention clip.

4. The method of claim 2, wherein the delivery tube is made of an easily bendable material and the method includes bending the delivery tube to improve access to the implant.

5. The method of claim 2, wherein the delivery tube is provided with a tensioning assembly on a proximal end thereof through which the free ends of the corresponding suture loop pass, and the method includes maintaining tension on the free ends using the tensioning assembly prior to displacing the elongated tension member.

6. The method of claim 2, wherein the elongated tension member and retention member are a single element defining a retention cable extending through multiple suture locking devices arranged in series within the delivery tube.

7. The method of claim 1, further including providing a suture snare having a distal loop thereon extending distally through each suture locking device, and the step of threading two free ends of each of the suture loops through each of the plurality of suture locking devices comprises passing the two free ends through the distal loop of the snare and withdrawing the snare proximally through the suture locking device so as to pull the free ends therethrough.

8. The method of claim 1, wherein the clamp halves are hinged together on a first circumferential side such that the variable sized slot defines a variable sized opening on the side opposite the first circumferential side, and wherein the biasing member comprises a plurality of C-clips arranged around the locking clamp with their free ends located on either side of the variable sized slot opposite the first circumferential side.

9. A method for anchoring a cardiac implant to a native valve annulus, the implant having been advanced to the native valve annulus down a plurality of loops of suture that are preinstalled at the native valve annulus, the sutures having a thickness, comprising:
providing an elongated delivery tool having a proximal end, a distal end, and a delivery tube therebetween having a lumen;
positioning a suture locking device on the distal end of the delivery tool, the suture locking device having a bifurcated locking clamp including a pair of substantially similar clamp halves each having an exterior surface and an inner surface facing the inner surface of the other clamp half, the clamp halves being fixed axially with respect to one another while being connected for movement toward or away from each other to form a variable sized slot having a width between the inner surfaces through which the free ends extend, wherein the device further includes a biasing member that, in the absence of an object in the slot, urges the inner surfaces of the clamp halves together such that the slot has a width smaller than the suture thickness, wherein the device has a retention member positioned between the clamp halves against the force of the biasing member with a thickness that maintains the slot width large enough to permit passage of a suture therethrough;
threading two free ends of one of the suture loops through the suture locking device;
advancing each suture locking device on the distal end of the delivery tube down the free ends of the suture loop until the locking device contacts the implant;
adjusting tension in the free ends of the suture loop passing through each locking device;
proximally pulling the retention member from between the clamp halves of the locking device, thus enabling the biasing member to force the clamp halves toward and clamp onto the free ends of the corresponding suture loop; and
repeating the preceding steps for each suture loop.

10. The method of claim 9, wherein the delivery tool includes an elongated tension member that extends along the delivery tube and that may be displaced axially from the proximal end, the step of assembling each suture locking device with a distal end of the delivery tube includes engaging a distal end of the elongated tension member with the retention member of that locking device, and the step of proximally pulling the retention member comprises displacing the elongated tension member so as to proximally pull the retention member from between the clamp halves of the device.

11. The method of claim 9, wherein the delivery tube is made of an easily bendable material and the method includes bending the delivery tube to improve access to the implant.

12. The method of claim 9, wherein the delivery tube is provided with a tensioning assembly on a proximal end thereof through which the free ends of the corresponding suture loop pass, and the method includes maintaining tension on the free ends using the tensioning assembly prior to displacing the elongated tension member.

13. The method of claim 9, further including providing a suture snare having a distal loop thereon extending distally through each suture locking device, and the step of threading two free ends of each of the suture loops through each of the plurality of suture locking devices comprises passing the two free ends through the distal loop of the snare and withdrawing the snare proximally through the suture locking device so as to pull the free ends therethrough.

14. The method of claim 9, wherein the clamp halves are hinged together on a first circumferential side such that the variable sized slot defines a variable sized opening on the side opposite the first circumferential side, and wherein the biasing member comprises a plurality of C-clips arranged around the locking clamp with their free ends located on either side of the variable sized slot opposite the first circumferential side.

15. A method for anchoring a cardiac implant to a native aortic valve annulus, the implant having been advanced to the aortic valve annulus down a plurality of loops of suture that are preinstalled at three locations around the aortic valve annulus, the three locations being aligned with the two coronary ostia CO and the non-coronary sinus, the sutures having a thickness, comprising:
providing three suture locking devices each having a bifurcated locking clamp including a pair of clamp halves fixed axially with respect to one another while being connected for movement toward or away from each other to form a variable sized slot having a width therebetween, each device further including a biasing member that urges the inner surfaces of the clamp halves together, each device further having a retention member positioned between the clamp halves against the force of the biasing member with a thickness that maintains the slot width large enough to permit passage of the suture free ends therethrough;
providing a suture snare having a distal loop thereon extending distally through each suture locking device;
threading two free ends of each of the suture loops through each of the plurality of suture locking devices by passing the two free ends through the distal loop of one of the snares and withdrawing the snare proximally through the corresponding suture locking device so as to pull the free ends therethrough;
advancing the suture locking devices down the free ends of the suture loops until the locking devices contact the implant;
adjusting tension in the free ends of the suture loop passing through each locking device;
proximally pulling the retention member from between the clamp halves of each locking device, thus enabling the biasing member to force the clamp halves toward and clamp onto the free ends of the corresponding suture loop; and further anchoring the cardiac implant to the native aortic valve annulus without using sutures, the three suture loops being the only sutures used to anchor the implant.

16. The method of claim 15, wherein the cardiac implant is a heart valve having a valve member and an expandable stent frame on an inflow end thereof, and wherein the step of further anchoring comprises expanding the stent frame outward against the native aortic valve annulus.

17. The method of claim 15, further including providing a suture snare having a distal loop thereon extending distally through each suture locking device, and the step of threading two free ends of each of the suture loops through each of the plurality of suture locking devices comprises passing the two free ends through the distal loop of the snare and withdrawing the snare proximally through the suture locking device so as to pull the free ends therethrough.

18. The method of claim 15, wherein the clamp halves are hinged together on a first circumferential side such that the variable sized slot defines a variable sized opening on the side opposite the first circumferential side, and wherein the biasing member comprises a plurality of C-clips arranged around the locking clamp with their free ends located on either side of the variable sized slot opposite the first circumferential side.

19. The method of claim 15, further including:
providing an elongated delivery tool having a proximal end and distal delivery tube, the tool further including an elongated tension member that extends along the delivery tube and that may be displaced axially from the proximal end;
assembling each suture locking device with a distal end of the delivery tube by engaging a distal end of the elongated tension member with the retention member of that locking device;
advancing each suture locking device on the distal end of the delivery tube down the free ends of the suture loop until the locking device contacts the implant; and
displacing the elongated tension member so as to proximally pull the retention member from between the clamp halves of the device on the distal end of the delivery tube, thus enabling the corresponding biasing member to force the clamp halves toward and clamp onto the free ends of the corresponding suture loop.

20. The method of claim 19, wherein the delivery tube is made of an easily bendable material and the method includes bending the delivery tube to improve access to the implant.

* * * * *